(12) United States Patent
Mahashabde et al.

(10) Patent No.: US 6,436,428 B1
(45) Date of Patent: Aug. 20, 2002

(54) DEVICE AND METHOD FOR TREATING URINARY INCONTINENCE IN FEMALES

(75) Inventors: Anu Mahashabde, Kendall Park; Martha Francine Kay, Lawrence Township, Mercer County; Donald F. Koelmel, Union Township, Hunterdon County, all of NJ (US)

(73) Assignee: Enhance Pharmaceuticals, Inc., Plainsboro, NJ (US)

(*) Notice: Subject to any disclaimer, the term of this patent is extended or adjusted under 35 U.S.C. 154(b) by 0 days.

(21) Appl. No.: 09/531,856

(22) Filed: Mar. 21, 2000

(51) Int. Cl.$^7$ .................................................. A61F 6/14
(52) U.S. Cl. ........................ 424/432; 924/486; 514/534
(58) Field of Search ........................... 514/534; 424/432, 424/486

(56) References Cited

U.S. PATENT DOCUMENTS

| | | |
|---|---|---|
| 4,286,587 A | 9/1981 | Wong |
| 4,402,695 A | 9/1983 | Wong |
| 5,411,740 A | 5/1995 | Lee et al. |
| 5,500,222 A | 3/1996 | Lee et al. |
| 5,532,278 A | 7/1996 | Aberg et al. |
| 5,601,839 A | 2/1997 | Quan et al. |
| 5,614,211 A | 3/1997 | Gale et al. |
| 5,626,866 A | 5/1997 | Ebert et al. |
| 5,674,895 A | * 10/1997 | Guittard et al. ............. 514/534 |
| 5,677,346 A | 10/1997 | Aberg et al. |
| 5,785,991 A | 7/1998 | Burkoth et al. |
| 5,834,010 A | 11/1998 | Quan et al. |
| 5,840,754 A | 11/1998 | Guittard et al. |
| 5,900,250 A | 5/1999 | Lee et al. |
| 5,912,268 A | 6/1999 | Guittard et al. |
| 5,972,372 A | * 10/1999 | Slaeh et al. .................. 424/432 |
| 6,056,976 A | * 5/2000 | Markkula et al. ........... 424/486 |
| 6,087,396 A | 7/2000 | Roberts |

FOREIGN PATENT DOCUMENTS

| | | |
|---|---|---|
| WO | 9323025 | 11/1993 |
| WO | 9811888 | 3/1998 |
| WO | 9924106 | 5/1999 |
| WO | 0019997 | 4/2000 |
| WO | 0020035 | 4/2000 |

* cited by examiner

Primary Examiner—Jose' G. Dees
Assistant Examiner—Robert DeWitty
(74) Attorney, Agent, or Firm—Gibbons, Del Deo, Dolan, Griffinger & Vecchione

(57) ABSTRACT

Provided herein is a novel and useful device and method for locally delivering and controllably releasing oxybutynin in the cervical region of a female. A device of the invention comprises a ring comprising trifluoropropylmethyl/dimethyl siloxane elastomer. A pharmaceutical composition comprising oxybutynin and an excipient is placed within a bore located in the ring, wherein the bore runs from the surface of the ring into the ring. The ring has a sufficient size such that it can be inserted into the vaginal canal of a female. A cap comprising is placed over the bore at the surface of the ring in order to contain the pharmaceutical composition within the bore. When the ring is inserted into the vaginal canal, the trifluoropropylmethyl/dimethyl siloxane elastomer controllably releases and locally delivers a therapeutically effective amount of oxybutynin to the detrusor muscle to treat the female's urinary incontinence.

21 Claims, 9 Drawing Sheets

☐ TFP

▨ PDMS

□ BARIUM SULFATE

PTFE TUBING WITH HORIZONTAL SLIT

PTFE TUBING WITH CURVED SLITS

DEVICE AND METHOD FOR TREATING URINARY INCONTINENCE IN FEMALES

FIELD OF THE INVENTION

The present invention relates to a new and useful device and method that utilizes trifluoropropylmethyl/dimethyl siloxane elastomer to locally deliver oxybutynin in a controlled manner for treating urinary incontinence for up to twenty-eight contiguous days, or as needed.

BACKGROUND OF THE INVENTION

Urinary incontinence is a debilitating disorder which afflicts at least 15% of the elderly population, and is present in approximately 50% of institutionalized elderly persons. Indeed, many elderly people are institutionalized because of their urinary incontinence. The costs for caring for such patients is extremely high, particularly since they require constant monitoring and changing of their clothes and bedding.

The elderly, however, are not the only group of the population that suffers from urinary incontinence. This disorder is also prevalent in postmenopausal women. In particular, pelvic relaxation due to childbirth can cause uterine prolapse and cystocele, which allows descent of the normal urethrovesical angle and contributes to urinary incontinence. The ramifications of the natural aging process in women, such as decreased levels of estrogen, also may result in urinary incontinence.

The therapeutic effect of oxybutynin (4-diethylamino-2-butynylphenylcyclohexylglycolate), which is described in the 1992 Physician's Desk Reference, pages 1332–1333 (with reference to the drug "DITROPAN" manufactured by Marion Merrill Dow), is well documented [Yarker, Y. E., Goe, K. L. & Fitton, A., Oxybutynin: A Review of its Pharmacodynamic and Pharmacokinetic Properties, and its Therapeutic Use in Detrusor Stability. Drugs & Aging 6(3):243–265 (1995)]. In particular, oxybutynin has an anticholinergic and spasmolytic effect on the bladder that leads to relaxation of the detrusor muscle, fewer spontaneous contractions, a decrease in the frequency and urge to urinate, and increased bladder-filling capacity.

Traditionally, oxybutynin has been administered orally at relatively high doses (5 mg tablets taken two to four times a day). Oxybutynin has also been incorporated into tablets, capsules, granules and pills containing 1–5 mg, preferably 5 mg of oxybutynin chloride, and syrups containing 1–5 mg, preferably 5 mg of oxybutynin chloride per 5 ml, and transdermal compositions (creams or ointments) containing 1–10 weight percent (wt %) oxybutynin chloride. Such administration techniques inherently permit oxybutynin to circulate throughout the body. Unfortunately however, oxybutynin has deleterious side effects when administered systemically. More specifically, anticholinergic side effects such as dry mouth, dry eyes, blurred vision, constipation, and headaches have been observed when oxybutynin is orally delivered. Moreover, N-desethyloxybutynin, a metabolite of oxybutynin produced in the liver, has similar antimuscarinic activity, and hence can have much of the same effects as oxybutynin both on the bladder's detrusor muscle and in other organs [Yarker, et al; Westlin, L., Anticholinergic Effects of Two Metabolites of Oxybutynin, Research Report No. 840625F, data on file, Smith and Nephew Pharmaceuticals, Ltd., 1985; Hughes, K. M., Lang, J. C. T., Lazare, R., et al., Measurement of Oxybutynin and its N-desethyl metabolite in Plasma, and its Application to Pharmacokinetic Studies in Young, Elderly and Frail Volunteers. Xenobiotica 22(7):859–69 (1992); Waldeck, K., Larsson, B., Andersson, K. E., Comparison of Oxybutynin and its Active Metabolite, N-desethyloxybutynin, in the Human Detrusor and Parotid Gland. Jnl. Of Urology 157:1093–97 (1997)]. Oral administration in particular has been shown to result in peak blood concentrations of the metabolite that are 6–9 times higher than the concentration of oxybutynin itself. Furthermore, the area under the plasma time concentration curve (or AUC, which measures the gross amount of drug present over time) is also higher for the metabolite (10–12 times) than for oxybutynin.

In order to ameliorate the effects of oxybutynin in the body and to limit the production of metabolite, efforts have been made to administer oxybutynin intravesically. Such delivery has demonstrated that oxybutynin can be delivered directly to the bladder of a patient, limit the circulation of oxybutynin in the body, and the deleterious side effects. However, intravesical delivery possesses inherent limitations. Initially, intravesical administration occurs through a catheter 3–4 times a day, and therefore is a cumbersome modality suited only to relatively immobile patients. Another limitation is that such delivery is uncomfortable to the patient. A major limitation of intravesical administration is that this method is simply not suited to frequent, long term use for most incontinence suffers.

Accordingly, what is needed is a new and useful device which delivers oxybutynin locally, i.e., directly to the detrusor muscle, in a controlled manner, and does not rely solely upon the body's circulatory system for such delivery. As a result, systemic circulation of oxybutynin and its metabolite to other body sites can be limited.

What is also needed is a new and useful device which is capable of locally delivering and controllably releasing a therapeutically effective amount of oxybutynin to a patient's detrusor muscle for up to twenty-eight (28) contiguous days. The citation of any reference herein should not be construed as an admission that such reference is available as "Prior Art" to the instant application.

SUMMARY OF THE INVENTION

There is provided, in accordance with the present invention, a device and method for locally delivering and controllably releasing a therapeutically effective amount of oxybutynin to the detrusor muscle in order to treat urinary incontinence in a female.

Broadly, the present invention extends to a device for locally delivering and controllably releasing oxybutynin to the cervical region of a female to treat urinary incontinence, wherein the device comprises a ring having a surface, and a bore running from the surface into the ring, wherein the ring comprises trifluoropropylmethyl/dimethyl siloxane elastomer. The ring of a device of the invention has a sufficient size such that it can be inserted into the vaginal canal of the female. Furthermore, a device of the invention comprises a pharmaceutical composition located within the bore, wherein the pharmaceutical composition comprises oxybutynin and an excipient. A device of the present invention also comprises a cap on the bore at the surface of the ring, wherein the cap prevents the pharmaceutical composition from diffusing out of the bore at the surface of the ring. Upon insertion of the ring into the vaginal canal, oxybutynin is controllably released from the ring in a therapeutically effective amount to treat the urinary incontinence.

A ring of a device of the invention can further comprise a first portion comprising trifluoropropylmethyl/dimethyl siloxane elastomer having a bore therein, and a second portion comprising a material into which oxybutynin is insoluble, such as a barium sulfate composite. A ring of a device of the invention can also comprise a first portion comprising trifluoropropylmethyl/dimethyl siloxane elastomer having a bore running from the surface of the first portion into the first portion, a second portion comprising polydimethylsiloxane elastomer, or a barium sulfate composite, and at least two shields located between the first and second portions, wherein the at least two shields comprise a material into which oxybutynin is insoluble, e.g., a barium sulfate composite or polytetrafluorethylene (PTFE). The two shields intersect the first and second portions, and prevent contact between the first and second portions. In a particular embodiment, the one bore intersects the surface of the first portion twice, and is capped at both ends with caps described above. As a result, the trifluoropropylmethyl/ dimethyl siloxane elastomer of the first portion controllably releases oxybutynin contained within the bore, and the barium sulfate composite shields prevent diffusion of oxybutynin to other parts of the ring. In another embodiment, wherein the first and second portions comprise trifluoropropylmethyl/dimethyl siloxane elastomer, the bore comprises a first bore which runs from the surface of the first portion into the first portion, and a second bore running from the surface of the second portion into the second portion. Optionally the bores can intersect the surface of the ring at two different points. Naturally, the cap of the invention comprises a sufficient number of caps to cover both bores, so that the pharmaceutical composition within the bore(s) is prevented from diffusing uncontrollably from the bore at the surface of the ring.

Alternatively, a ring of a device of the invention comprises four portions and four shields such that each shield intersects two portions, and each portion is prevented from contacting any other portion. At least one of the portions comprises trifluoropropylmethyl/dimethyl siloxane elastomer having a bore running from the surface of the portion into the portion. Other portions of the ring can comprise polydimethylsiloxane, barium sulfate composite, or a combination thereof.

In addition, the present invention extends to a device for locally delivering and controllably releasing oxybutynin as described above, wherein the amount of oxybutynin in the pharmaceutical composition can vary, depending upon the desired dose to be administered to the patient. In a particular embodiment, the pharmaceutical composition comprises about 60% by weight oxybutynin and about 40% by weight an excipient, e.g., tin catalyzed silicone polymer. Naturally, the oxybutynin can be in a free base form, a salt, or a mixture thereof. Optionally, the pharmaceutical composition comprises a rod which is inserted into the one bore(s) of the ring. Methods of producing such rods are described infra. A therapeutically effective amount of oxybutynin that can be locally delivered with a device of the invention ranges from about 0.5 mg/day to about 5.0 mg/day as needed. In a particular embodiment, a device of the present invention can locally deliver a therapeutically effective amount of oxybutynin for up to twenty-eight contiguous days.

Moreover, the present invention extends to a device as described above, wherein caps are placed over the bore at the surface of the ring. Consequently, an oxybutynin pharmaceutical composition can be held within the bore of a ring of a device of the invention, and come into direct contact with the trifluoropropylmethyl/dimethyl siloxane elastomer of the ring, and be contained within the bore. Numerous materials can serve as caps in a ring of a device of the invention. Particular examples of such materials include, but certainly are not limited to trifluoropropylmethyl/dimethyl siloxane elastomer, and polydimethylsiloxane (PDMS), to name only a few.

In another embodiment, the present invention extends to a device for locally delivering and controllably releasing oxybutynin to the cervical region of a female to treat urinary incontinence, wherein the device comprises:

(a) a ring having a surface, and a bore which runs from the surface into the ring, wherein the ring comprises trifluoropropylmethyl/dimethyl siloxane elastomer, and the ring has a sufficient size such that it can be inserted into the vaginal canal of the female;

(b) a pharmaceutical composition located within the bore, wherein the pharmaceutical composition comprises 60% by weight oxybutynin and 40% by weight tin catalyzed silicone polymer;

(c) a cap which covers the bore at the surface of the ring, wherein the cap comprises polydimethylsiloxane, such that upon insertion of the ring into the vaginal canal, the oxybutynin is controllably released from the ring in a therapeutically effective amount to treat the urinary incontinence. Optionally, the bore intersects the surface of the ring twice, and thus requires two caps, one to cover the bore at each point it intersects the surface of the ring.

The present invention further extends to a method for locally delivering and controllably releasing a therapeutically effective amount of oxybutynin in the cervical region of a female to treat urinary incontinence. An initial step of a method of the invention comprises providing a ring having a surface, and a bore running from the surface into the ring. A pharmaceutical composition comprising oxybutynin and an excipient is located within the bore. Moreover, the ring comprises of trifluoropropylmethyl/dimethyl siloxane elastomer, which controllably releases oxybutynin, and has a sufficient size such that it can be inserted into the vaginal canal of the female. Furthermore, a ring of a method of the invention comprises a cap which covers the bore at the surface of the ring, so that the pharmaceutical composition is contained within the bore. The ring is then inserted into the vaginal canal of the female. Once in the vaginal canal, a therapeutically effective amount of oxybutynin is controllably released from the ring, and treats the female's urinary incontinence.

In addition, the present invention extends to a method of treating urinary incontinence in a female as described above, wherein the ring comprises a first portion comprising trifluoropropylmethyl/dimethyl siloxane elastomer, a second portion comprising a barium sulfate composite or polydimethylsiloxane, and the bore runs from the surface of the first portion into the first portion of the ring.

The present invention further extends to a method of treating urinary incontinence in a female, wherein the ring comprises at a first portion comprising trifluoropropylmethyl/dimethyl siloxane elastomer, a second portion comprising trifluoropropylmethyl/dimethyl siloxane elastomer, a barium sulfate composite or polydimethylsiloxane, and at least two shields comprising a material into which oxybutynin is insoluble, .e.g., a barium sulfate composite or polytetrafluoroethylene, wherein the at least two shields are located between the first and second portions and prevent contact between the first and second portions. The bore runs from the surface of the first portion into the first portion. Furthermore, a method of the invention extends to a ring comprising a first bore running from the surface of the first portion into the first portion, and intersecting the surface of the first portion twice. Additionally, in a ring in which the second portion comprises trifluoropropylmethyl/dimethyl siloxane elastomer, the ring further comprises a second bore which runs from the surface of the second portion into the second portion. Optionally, the second bore intersects the surface of the second portion twice. Naturally, a sufficient number of caps comprising a material such as trifluoropropylmethyl/dimethyl siloxane elastomer, polydimethylsiloxane, polytetrafluoroethylene, etc. are used in a ring of a method of the invention to cover the bore(s) at intersection points with the surface of the ring so that the pharmaceutical composition is contained within the bore(s).

As explained above, a pharmaceutical composition of a method of the invention comprises oxybutynin and an excipient, such as tin catalyzed silicone polymer. The therapeutically effective amount of oxybutynin locally delivered and controllably released with a method or device of the invention can vary, depending upon the particular needs of the patient. In a particular embodiment, the pharmaceutical composition comprises about 60% by weight oxybutynin and about 40% by weight excipient, such as tin catalyzed silicone polymer. Such a composition can be used to locally deliver and controllably release a therapeutically effective amount of oxybutynin ranging from about 0.5 mg/day to about 5 mg/day, for up to 28 days. Data of delivery of oxybutynin for 28 contiguous days is set forth in FIG. 5.

In another embodiment, the present invention extends to a method for locally delivering and controllably releasing a therapeutically effective amount of oxybutynin in the cervical region of a female to treat urinary incontinence, comprising the steps of:

(a) providing a ring comprising polydimethylsiloxane, trifluoropropylmethyl/dimethyl siloxane elastomer, a barium sulfate composite, or a combination thereof, wherein the ring has a sufficient size such that it can be inserted into the vaginal canal of the female, and comprises a bore in the trifluoropropylmethyl/dimethyl siloxane elastomer which runs from the surface of the ring into the ring, (b) inserting a pharmaceutical composition comprising oxybutynin and an excipient weight tin catalyzed silicone polymer within the bore;

(c) placing a cap on the bore at the surface of the ring; and (d) inserting the ring into the vaginal canal of the female.

Once in the vaginal canal, a therapeutically effective amount of oxybutynin ranging from about 0.5 mg/day to about 5 mg/day is controllably released from the ring for up to twenty eight days. A ring having applications herein can comprise a first portion comprising trifluoropropylmethyl/dimethyl siloxane elastomer, and a second portion comprising a barium sulfate composite, polydimethylsiloxane or trifluoropropylmethyl/dimethyl siloxane elastomer, wherein the bore runs from the surface of the first portion into the first portion. Optionally, the bore intersects the surface of the first portion twice. Furthermore, in a ring comprising a second portion which comprises trifluoropropylmethyl/dimethyl siloxane elastomer, the bore further comprises a second bore which runs from the surface of the second portion into the second portion. Pharmaceutical composition is contained within both bores. Optionally, the second bore intersects the surface of the second portion twice. Naturally, a ring of a device of the invention comprises a sufficient number of caps to cover the points of intersection between the surface and the bore(s) so that the pharmaceutical composition is contained within the bore(s).

Moreover, a ring having applications in a method of the invention can comprise a first and a second portion, and at least two shields comprising a pharmaceutically acceptable inert material into which oxybutynin is insoluble, such as a barium sulfate composite or polytetrafluoroethylene. At least two shields are located between the first and second portions, and prevent contact between these two portions. In a particular embodiment, the first portion comprises trifluoropropylmethyl/dimethyl siloxane elastomer, and the second portion comprises trifluoropropylmethyl/dimethyl siloxane elastomer, polydimethylsiloxane, or a barium sulfate composite. The bore comprises a first bore located in the first portion. Optionally, the first bore intersects the surface of the first portion twice. Furthermore, if the second portion comprises trifluoropropylmethyl/dimethyl siloxane elastomer, the bore further comprises a second bore which runs from the surface of the second portion into the second portion. Optionally, the second bore intersects the surface of the second portion twice. Naturally, a sufficient number of caps are used to cover the intersection points of the bore(s) and the surface of the ring in order to contain the pharmaceutical composition within the bore(s).

Furthermore, the present invention extends to a method for locally delivering and controllably releasing a therapeutically effective amount of oxybutynin in the cervical region of a female to treat urinary incontinence, as described above, wherein the ring comprises first and second portions, and at least two shields into which oxybutynin is insoluble. The at least two shields are located between the first and second portions of the ring, and prevent contact between the first and second portions. Examples of substances which form such shields include a barium sulfate composite or polytetrafluoroethylene, to name only a few. Either the first portion, the second portion or both portions of the ring can comprise trifluoropropylmethyl/dimethyl siloxane elastomer. Moreover, when the second portion of the ring also comprises trifluoropropylmethyl/dimethyl siloxane elastomer, the bore further comprises a second bore which runs from the surface of the second portion into the second portion. Optionally, the bore intersects the first portion twice, and the second bore intersects the surface of the second portion twice. Naturally, a sufficient number of caps as described above are used to cover the intersection points of the bore(s) and the surface of the ring in order to contain the pharmaceutical composition within the bore(s).

The present invention further extends to a method for locally delivering and controllably releasing a therapeutically effective amount of oxybutynin in the cervical region of a female to treat urinary incontinence, as described above, wherein the pharmaceutical composition comprises about 60% by weight oxybutynin and about 40% by weight an excipient, preferably tin catalyzed silicone polymer. In a particular embodiment, the pharmaceutical composition is in the shape of a rod, which is inserted into the bore of the ring.

Accordingly, it is a principal object of the present invention to provide a device and method for treating urinary incontinence which locally delivers and controllably releases oxybutynin in the cervical region of a female so that the oxybutynin can diffuse directly to, and interact with the detrusor muscle.

It is another object of the present invention to utilize the heretofore unknown ability of trifluoropropylmethyl/dimethyl siloxane elastomer to controllably release oxybutynin.

It is still another object of the invention to provide a device and method for treating urinary incontinence which locally delivers and controllably releases a therapeutically effective amount of oxybutynin to the female for up to twenty-eight contiguous days.

It is yet another object of the invention to provide a device and method for treating urinary incontinence wherein the therapeutically effective amount of oxybutynin delivered to the patient can be tailored to the patient's needs.

These and other aspects of the present invention will be better appreciated by reference to the following drawings and Detailed Description.

DETAILED DESCRIPTION OF THE INVENTION

Figure 1A:
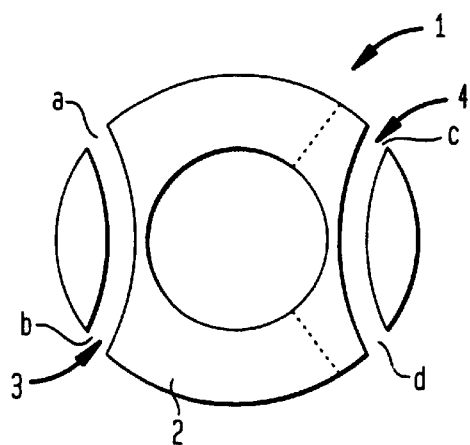
FIG. 1A is a schematical cross sectional view of a ring of a device of the invention.

The present invention is based upon the discovery that surprisingly and unexpectedly, trifluoropropylmethyl/dimethyl siloxane elastomer controllably releases oxybutynin when an oxybutynin pharmaceutical composition is inserted within trifluoropropylmethyl/dimethyl siloxane elastomer. Thus, a device comprising, inter alia, trifluoropropylmethyl/dimethyl siloxane elastomer surrounding oxybutynin, that is inserted into the vaginal canal of the female, controllably releases and locally delivers a therapeutically effective of amount of oxybutynin to the detrusor muscle of a female for up to 28 contiguous days. As a result, circulation of oxybutynin and its metabolite N-desethyloxybutynin throughout the body is largely avoided, along with the side effects that have traditionally been associated with such circulation.

In particular, the present invention extends to a device for locally delivering and controllably releasing oxybutynin to the cervical region of a female to treat urinary incontinence, comprising:

(a) a ring having a bore running from the surface of the ring, wherein the ring comprises trifluoropropylmethyl/ dimethyl siloxane elastomer, and has a sufficient size such that it can be inserted into the vaginal canal of the female;

(b) a pharmaceutical composition located within the bore, wherein the pharmaceutical composition comprises oxybutynin and an excipient; and (c) a cap placed on the bore at the surface of the ring so that the pharmaceutical composition is contained within the bore, such that upon insertion of the ring into the vaginal canal, oxybutynin is controllably released from the ring in a therapeutically effective amount, and locally delivered to treat urinary incontinence.

Furthermore, the present invention extends to a device for locally delivering and controllably releasing oxybutynin to the cervical region of a female to treat urinary incontinence, the device comprising:

(a) a ring having a bore running from the surface of the ring, wherein the ring comprises a pharmaceutically acceptable inert material that controllably releases oxybutynin, and has a sufficient size such that it can be inserted into the vaginal canal of the female; and (b) a pharmaceutical composition rod comprising oxybutynin and an excipient, wherein the rod is inserted into the bore, (c) a cap comprising the pharmaceutically acceptable inert material that is placed on the bore at the surface of the ring so that the pharmaceutical composition is contained within the bore, such that upon insertion of the ring into the vaginal canal, oxybutynin is controllably released from the ring in a therapeutically effective amount, and locally delivered to treat urinary incontinence.

Furthermore, the present invention extends to a method for locally delivering and controllably releasing a therapeutically effective amount of oxybutynin in the cervical region of a female to treat urinary incontinence, comprising the steps of:

(a) providing a ring having at least one bore running from the surface of the ring, wherein the ring comprises trifluoropropylmethyl/dimethyl siloxane elastomer which controllably releases oxybutynin, and has a sufficient size such that it can be inserted into the vaginal canal of the female;

(b) inserting a pharmaceutical composition comprising oxybutynin and excipient into the bore;

(c) placing a cap on the bore at the surface of the ring so that the pharmaceutical composition is contained within the bore, and (d) inserting the ring into the vaginal canal, so that a therapeutically effective amount of oxybutynin is controllably released from the ring to treat the urinary incontinence.

Numerous terms and phrases are used regularly throughout the instant specification and appending claims. Accordingly, as used herein, the term "oxybutynin" refers to oxybutynin the base, optically resolved oxybutynin, and related compounds (e.g., salts) thereof. Oxybutynin is a base capable of forming salts with organic and mineral acids, for example, with hydrochloric acid to form oxybutynin chloride. A particular form of oxybutynin having applications in a device and method of the present invention is oxybutynin base.

As used herein, the term "excipient" refers to a pharmaceutically acceptable diluent, adjuvant, carrier, or vehicle with which oxybutynin is administered. Such excipients can be sterile liquids, including those of petroleum, animal, vegetable or synthetic origin, such as peanut oil, soybean oil, mineral oil, sesame oil and the like. A particular example of an excipient having applications herein comprises tin catalyzed silicone polymer.

As used herein, the singular forms "a," "an" and "the" include plural referents unless the context clearly dictates otherwise.

As used herein, the phrase "at least one" means one or more than one.

As used herein, the phrase "vaginal canal" refers to a canal which runs from the hymenal ring to the cervix of a female (also referred to as the vagina) and the fornices surrounding the vagina.

As used herein, the term "biocompatible" refers to a material having the property of being biologically compatible by not producing a toxic, injurious, or immunological response in living tissue.

As used herein, the phrase "pharmaceutically acceptable" refers to molecular entities, excipients, and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the US Pharmacopoeia or other generally recognized pharmacopoeia for use in animals, and more particularly in humans.

The phrase "therapeutically effective amount" as used herein refers to an amount of oxybutynin sufficient to alleviate urinary incontinence by at least about 15 percent, preferably by at least 50 percent, more preferably by at least 90 percent, and most preferably prevent urinary incontinence in the patient.

As used herein, the phrase "locally deliver" refers to delivering oxybutynin directly to the cervical region of the female so that it can interact with the detrusor muscle. Such delivery is not dependent upon the patient's circulatory or digestive systems.

As used herein, the phrase "controllably released" refers generally to the release of oxybutynin from a ring of the invention, wherein the excipient and/or the trifluoropropylmethyl/dimethyl siloxane elastomer of the ring retard the release of oxybutynin in order to prevent immediate release of all the oxybutynin in the pharmaceutical composition to the cervical region. In a particular embodiment, the release of oxybutynin ranges from about 0.5 mg/day to about 5 mg/day for up to twenty-eight contiguous days.

As used herein, the term "detrusor muscle" refers to the external longitudinal layer of the muscular coat of the bladder. Contraction of the detrusor muscle is involved in emptying of the bladder and urination. Relaxation of the detrusor permits the bladder to fill with urine prior to urination.

As used herein, the phrase "urinary incontinence" refers to the disorder of lacking normal voluntary control of excretory urinary functions. Urinary incontinence includes: overflow incontinence, which involves contractile dysfunction of the detrusor muscle and results in large bladder volumes and urinary dribbling; stress incontinence, wherein patients lose small volumes of urine as a result of temporarily increased abdominal pressure; and functional incontinence, which is present in normally continent individuals as a result of physical or cognitive problems, or various medications, e.g., diuretics. A device or method of the present invention can readily be used to treat any of these particular types of urinary incontinence.

As used herein, the phrase "barium sulfate composite" refers a composite comprising barium sulfate and a siloxane polymer. A particular example of a barium sulfate composite having applications herein comprises about 48% by weight barium sulfate ($BaSO_4$) and about 52% by weight polydimethylsiloxane (PDMS).

As used herein, the phrase "trifluoropropylmethyl/ dimethyl siloxane elastomer" refers to an elastomer having a chemical formula of:

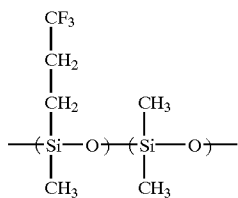

As explained above, a device of the invention comprises a ring having a bore in the surface of the ring. FIG. 1A schematically shows a ring (1) of a device of the invention in which the bore comprises two bores which run from the surface of the ring into the ring, and intersect the surface of the ring twice. In particular, ring (1) comprises a surface (2). A first bore (3) runs from surface (2) into ring (1). Furthermore, bore (3) intersects surface (2) of ring (1) at points a and b. A second bore (4) also runs from surface (2) of ring (1) into ring (1). Also, just as with bore (3), bore (4) intersects surface (2) twice, i.e, at c and d. As explained above, ring (1) comprises a pharmaceutically acceptable inert material that controllably releases oxybutynin, such as trifluoropropylmethyl/dimethyl siloxane elastomer. A device of the invention also comprises pharmaceutical composition comprising oxybutynin and an excipient, which is placed within bore (3) and/or (4). The oxybutynin can be in a free base form, a salt form, or a mixture thereof. In a particular embodiment, the pharmaceutical composition comprises about 60% by weight oxybutynin, and about 40% by weight excipient. Furthermore, a particular excipient having applications herein comprises tin catalyzed silicone polymer. Caps (not shown) comprising trifluoropropylmethyl/ dimethyl siloxane elastomer, polydimethylsiloxane, or polytetrafluoroethylene are placed on the bores at points a–d after the pharmaceutical compostion is placed in the bores, and prior to insertion of the ring into the vaginal canal.

Figure 1B:
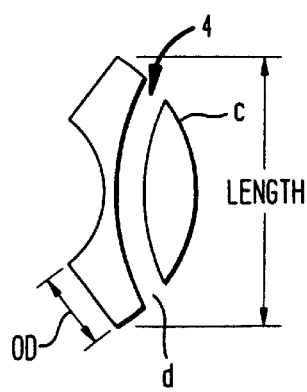
FIG. 1B is a schematical cross sectional view of a portion of a ring of a device of the invention, wherein the portion comprises a bore which runs from the surface of the portion, into the ring, and intersects the surface of the portion twice.

FIG. 1(b) schematically shows a cross section of a portion of ring (1) which comprises bore (4). As explained above, a device of the invention has applications in a variety of females, including, but not limited to human, bovine, feline, canine, equine or porcine females, to name only a few. Thus, the size and dimensions of the ring and the bore(s) will vary, so that the ring has sufficient size to be inserted into the vaginal canal of the female. FIG. 1(b) schematically shows a ring of a particular embodiment of a device of the invention, wherein the female is a human. The cross-sectional diameter of ring (1) is about 8.5 mm±0.5 mm.

Moreover, bore (3) has an outer diameter of about 3.2 mm, and a length of about 2.2 cm.

Figure 6A:
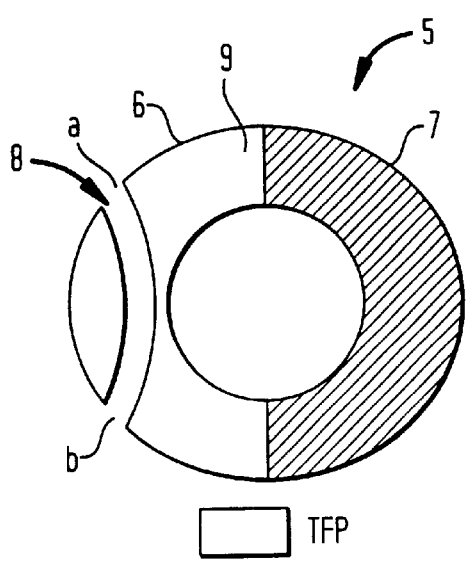
FIG. 6A is a schematical cross sectional view of a ring of a device of the invention comprising one portion trifluoropropylmethyl/dimethyl siloxane elastomer, and one portion polydimethysiloxane, wherein the bore is located in the trifluoropropylmethyl/dimethyl siloxane elastomer portion.

FIG. 6A is a schematical view of a ring of a device of the invention, wherein ring (5) comprises a first portion (6) comprising trifluoropropylmethyl/dimethyl siloxane elastomer, and a second portion (7) comprising polydimethylsiloxane. The bore (8) runs from surface (9) of first portion (6) into first portion (6) of the ring. In a particular embodiment as schematically shown in FIG. 6, bore (8) runs from surface (9) of first portion (6) into first portion (6), and intersects surface (9) at a and b.

Figure 7A:
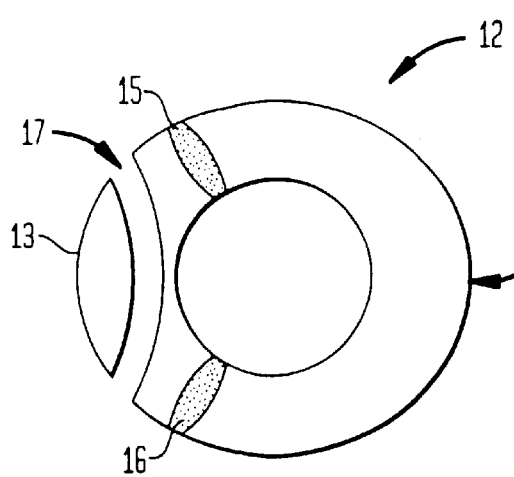
FIG. 7A is a schematical view of a ring of the invention comprising two shields into which oxybutynin is insoluble.
Figure 7B:
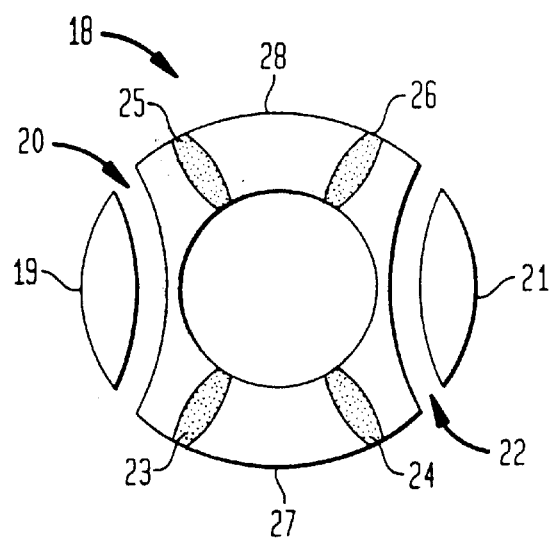
FIG. 7B is a schematical view of a ring of a device of the invention comprising 4 shields into which oxybutynin is insoluble.

Furthermore, the present invention extends to a device for locally delivering and controllably releasing oxybutynin in the vaginal canal of a female as described above, wherein a ring of a device of the invention comprises, inter alia, a first portion, a second portion, and at least two shields comprising a material into which oxybutynin is substantially insoluble. The at least two shields lie between the first and second portions, and prevent contact between the first and second portions. FIGS. 7A and 7B provide schematical cross sectional views of such rings. In particular, ring (12) of FIG. 7A comprises a first portion (13), a second portion (14) and two shields (15) and (16). Bore (17) runs from the surface of first portion (13) into first portion (13) and intersects the surface of portion (13) at two places. Portion (13) comprises a pharmaceutically acceptable inert material that controllably releases oxybutynin, e.g., trifluoropropylmethyl/ dimethyl siloxane elastomer. Portion (14) can be comprised of a variety of materials, including but not limited to polydimethylsiloxane, polytetrafluoroethylene, trifluoropropylmethyl/dimethyl siloxane elastomer, a barium sulfate composite, or a mixture thereof. Shields (15) and (16), located between portions (13) and (14), prevent contact between portions (13) and (14). When a pharmaceutical composition comprising oxybutynin and an excipient is placed within bore (17), shields (15) and (16) substantially limit diffusion of oxybutynin into ring (12) beyond portion (13). Thus, when ring (12) is inserted into the vaginal canal of a female, the trifluoropropylmethyl/dimethyl siloxane elastomer portion of the ring controllably releases oxybutynin to treat incontinence.

FIG. 7(B) schematically shows another embodiment of a ring of a device of the invention. In particular, ring (18) of FIG. 7B comprises first portion (19) with a first bore (20) in first portion (19), and a second portion (21) with bore (22) therein. Ring (18) further comprises portions (27) and (28), four shields (23), (24), (25), and (26). Shields (23)–(26) are located between first and second portions (19) and (21) respectively, and prevent contact between first and second portions (19) and (20). As explained above, ring (18) can be comprised of numerous materials, including, but not limited to polydimethylsiloxane, polytetrafluoroethylene, trifluoropropylmethyl/dimethyl siloxane elastomer, a barium sulfate composite, or a combination thereof, to name just a few. In the embodiment schematically shown in FIG. 7B, portions (19) and (21) comprise trifluoropropylmethyl/ dimethyl siloxane elastomer, and portions (27) and (28) comprise trifluoropropylmethyl/dimethyl siloxane elastomer, polytetrafluoroethylene, polydimethylsiloxane, a barium sulfate composite, or a combination thereof. The cross-sectional diameter of ring (18) is about 8.5 mm±0.5 mm. Moreover, bores (20) and (22) have an outer diameter of about 3.2 mm, and a length of about 2.2 cm.

Referring again to FIG. 7(B), shields (23)–(26) comprise polytetrafluoroethylene. A pharmaceutical composition comprising oxybutynin and a tin catalyzed silicone polymer excipient is placed within bores (20) and/or (22) of ring (18).

Caps (not shown) are then placed over the bores at the surface of the ring in order to contain the pharmaceutical composition within the bore. Ring(18) is then inserted into the vaginal canal of a female. Oxybutynin diffuses from the pharmaceutical composition and then through the trifluoropropylmethyl/dimethyl siloxane elastomer portion of the ring, which in turn controllably releases the oxybutynin in order to alleviate the female's urinary incontinence.

Figure 8A:
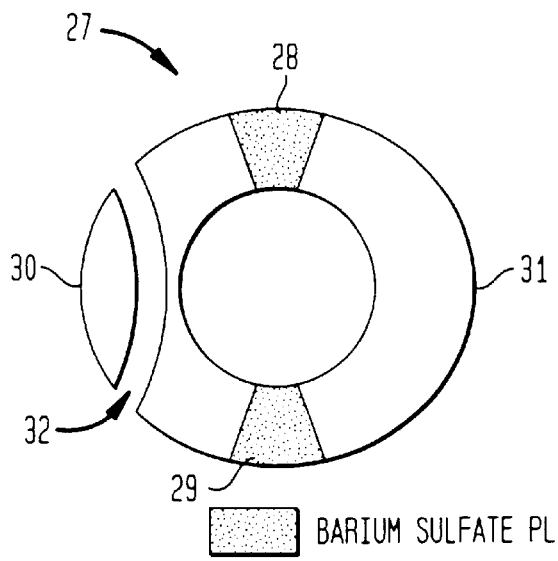
FIG. 8A is a schematical cross sectional view of a ring of a device of the invention comprising a first portion of trifluoropropylmethyl/dimethyl siloxane elastomer, a second portion comprising PDMS, and shields comprising a barium sulfate composite, wherein the shields located between the first and second portions, which prevent contact between the first and second portions.

FIGS. 8A and B schematically show other embodiments or a ring of a device of the invention, wherein the ring comprises two portions and at least two shields located between the portions. Oxybutynin is substantially insoluble in the shields. Thus, the shields prevent contact between the portions and limit any diffusion of oxybutynin from the portion of the ring with the bore containing the pharmaceutical composition to other portions of the ring. As schematically shown in FIG. 8A, ring (27) comprises trifluoropropylmethyl/dimethyl siloxane elastomer. Thus, first portion (30) and second portion (31) comprise trifluoropropylmethyl/dimethyl siloxane elastomer. A first shield (28) and a second shield (29) comprising a barium sulfate composite lie between lie between first portion (30) and second portion (31) of ring (27), and prevent contact between portions (30) and (31). A bore (32) is located in first portion (31) and intersects with the surface of first portion (31) twice. As a result, ring (27) comprises a combination of trifluoropropylmethyl/dimethyl siloxane elastomer and a barium sulfate composite. A pharmaceutical composition comprising oxybutynin and an excipient, e.g., tin catalyzed silicone polymer is placed within bore (32). Caps (not shown) are then placed over the points of intersection of the bores and the outer surfaces of the ring. These caps can be comprised of numerous materials, including trifluoropropylmethyl/dimethyl siloxane elastomer, polytetrafluoroethylene, or polydimethylsiloxane. In a particular embodiment, the caps comprise polydimethylsiloxane. Since oxybutynin is substantially insoluble in barium sulfate composite shields (28) and (29), it is sequestered in first portion (30), and is unable to diffuse throughout ring (27). When ring (27) is inserted into the vaginal canal of a female, the trifluoropropylmethyl/dimethyl siloxane elastomer controllably releases oxybutynin. The controllably released oxybutynin interacts with the female's detrusor muscle, and treats the female's urinary incontinence.

Figure 8B:
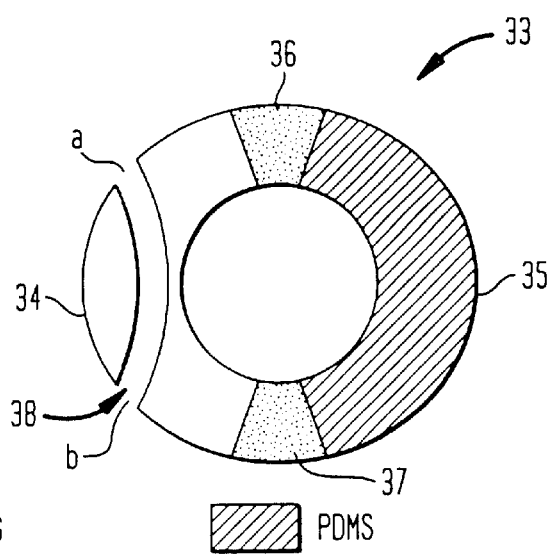
FIG. 8B is a schematical cross sectional view of a ring of a device of the invention comprising a first portion of trifluoropropylmethyl/dimethyl siloxane elastomer, a second portion comprising PDMS, and first and second shields between the first and second portions that prevent contact between the first and second portions.

FIG. 8B schematically shows a ring of a device of the invention which comprises a combination of materials. In particular, ring (33) schematically shown in FIG. 8B comprises a first portion (34) of trifluoropropylmethyl/dimethyl siloxane elastomer, a second portion (35) comprising polydimethylsiloxane, and two barium sulfate composite shields (36) and (37) located between first portion (34) and second portion (35). Shields (36) and (37) prevent contact between first and second portions (34) and (35). A bore (38), located in first portion runs from the surface of first portion (34) into portion (34), and intersects the surface of first portion (34) at a and b. A pharmaceutical composition comprising oxybutynin and tin catalyzed silicone polymer excipient is then placed in bore (38). When ring (33) is inserted into the vaginal canal of a female, oxybutynin is controllably released from the ring and interacts with the female's detrusor muscle.

As explained above, a device of the invention can be used to treat urinary incontinence in a variety of females, including, but not limited to human, bovine, porcine, equine, canine, and feline females, to name only a few. In a particular embodiment, the female is human. Thus, when used in a human female, a ring of a device of the invention would have a cross sectional diameter of about 8.5 mm±0.5 mm, and a ring diameter of about 5.5±0.1 cm. The outer diameter and length of a bore of a ring of the invention, such as the bore schematically shown in FIGS. 8A and 8B for example, is about 3.2 mm and about 2.2 cm respectively.

Figure 9:
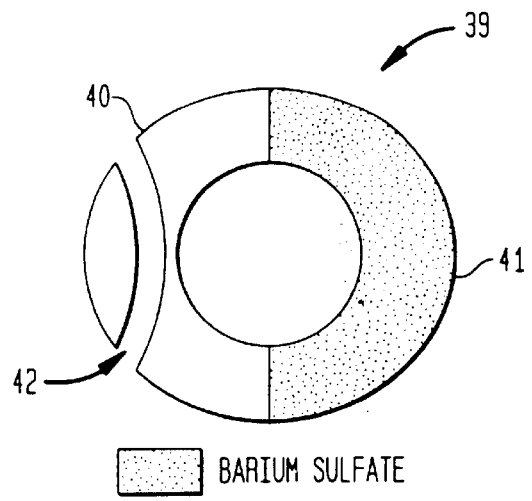
FIG. 9 is a schematical cross sectional view of a ring of a device of the invention comprising a first portion of trifluoropropylmethyl/dimethyl siloxane elastomer and a second portion comprising a barium sulfate composite, wherein the at least one bore comprises a bore in the first portion.

FIG. 9 schematically shows another example of a ring of a device of the invention comprising a combination of materials. More specifically, FIG. 9 schematically shows a cross sectional view of ring (39) which comprises a first portion (40) of trifluoropropylmethyl/dimethyl siloxane elastomer and a second portion (41) comprising a barium sulfate composite. A bore (42), located in first portion (40), intersects the surface of first portion (40) twice, and runs into first portion (40). A pharmaceutical composition comprising about 60% by weight oxybutynin and about 40% tin catalyzed silicone polymer excipient is then inserted into bore (42). In a particular embodiment, the pharmaceutical composition is formed into a rod as described infra. The rod is then inserted into bore (42). The amount of pharmaceutical composition placed in bore (42) can vary, depending upon the desired therapeutically effective amount of oxybutynin to be delivered.

FIG. 10 provides a schematical cross sectional view of a portion of a ring of the invention comprising trifluoropropylmethyl/dimethyl siloxane elastomer, wherein the portion comprises a bore and a pharmaceutical composition comprising about 60% by weight oxybutynin and about 40% by weight tin catalyzed silicone polymer excipient in the bore. Numerous methods for preparing a pharmaceutical composition comprising oxybutynin and tin catalyzed silicone polymer excipient are readily available to one of ordinary skill in the art, and have applications in a device of the present invention. A particular method of the present invention comprises forming rods of the pharmaceutical composition. In particular, polytetrafluoroethylene tubing having a diameter of about 3.2 mm is provided. Slits are then put into the tubing. Examples of such slits are schematically shown in FIGS. 10D and 10E.

After the slits are placed in the tubing, the tubing is filled with a pharmaceutical composition comprising oxybutynin and tin catalyzed silicone polymer as an excipient. The pharmaceutical composition within the tubing is then cured at about room temperature for about twenty-four (24) hours.

Figure 10A:
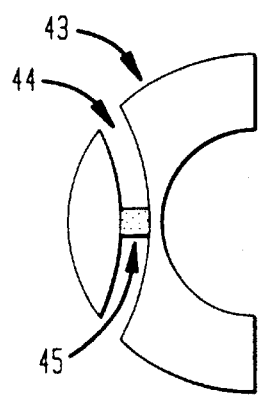
FIG. 10A is a schematical cross sectional view of a portion of a ring of a device of the invention schematically showing a pharmaceutical composition comprising oxybutynin and a silicone excipient in a bore in the ring, wherein the pharmaceutical composition contains sufficient oxybutynin to deliver about 0.5 mg/day.
Figure 10B:
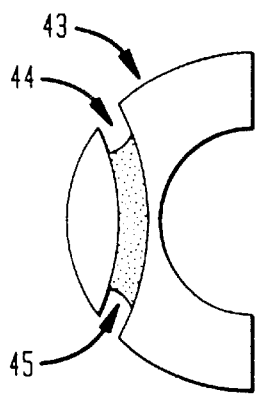
FIG. 10B is a schematical cross sectional view of a portion of a ring of a device of the invention schematically showing a pharmaceutical composition comprising oxybutynin and a silicone excipient in a bore in the ring, wherein the pharmaceutical composition contains sufficient oxybutynin to deliver about 1.0 mg/day.
Figure 10C:
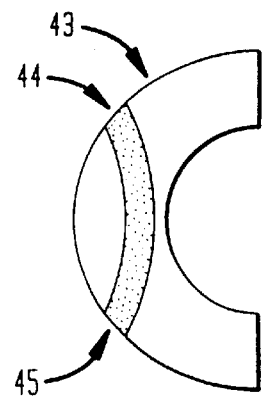
FIG. 10C is a schematical cross sectional view of a portion of a ring of a device of the invention schematically showing a pharmaceutical compostion comprising oxybutynin and a silicone excipient in a bore in the ring, wherein the pharmaceutical composition contains sufficient oxybutynin to deliver about 5.0 mg/day.
Figure 10D:
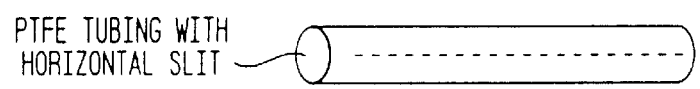
FIG. 10D shows a side view of polyterafluoroethylene tubing with exemplary slits parallel to the tubing which may be used in the present invention to form pharmaceutical composition rods.

After curing, the polytetrafluoroethylene tubing is removed, leaving a pharmaceutical composition rod comprising oxybutynin and tin catalyzed silicone polymer that can readily be inserted into a bore in a ring of a device of the invention. Such rods also permit medical providers to place an appropriate amount of pharmaceutical composition into a bore in a ring of a device of the invention in order to locally deliver and controllably release a particular therapeutically effective amount of oxybutynin. More specifically, FIGS. 10A–C schematically show a trifluoropropylmethyl/dimethyl siloxane elastomer portion (44) of a ring for use in a human female, wherein the ring has a cross sectional diameter of about 8.5 mm±0.5 mm, and a ring diameter of about 5.5±0.1 cm. A bore (44) runs from the surface of portion (44) into portion (44), and intersects the surface of portion (44) twice. The diameter of bore (44) is about 3.2 mm, and bore (44) has a length of about 2.2 cm. Pharmaceutical composition (45) comprising about 60% by weight oxybutynin and about 40% by weight tin catalyzed silicone polymer that was formed into a rod as described above, is inserted into bore (44). In FIG. 10A, approximately 0.55 cm of a rod of pharmaceutical composition is schematically shown inserted into bore (44). This length of rod has been determined sufficient to locally deliver and controllably release approximately 0.5 mg/day of oxybutynin in the vaginal canal of a human female for up to twenty-eight days. Likewise, FIGS. 10(A) and 10(B) respectively schematically show that approximately 1.65 cm of pharmaceutical composition of rod inserted into bore (44) delivers about 1.0 mg/day of oxybutynin, and 2.2 cm of pharmaceutical composition rod delivers approximately 5.0 mg/day of oxybutynin.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Urinary incontinence is a debilitating disorder that causes unwanted suffering and embarrassment to its victims. Oxybutynin, a drug used to treat urinary incontinence has traditionally been delivered via oral ingestion, and transdermally. However, such methods have inherent limitations, particularly since these methods are dependent upon a patient's gastrointestinal, and/or circulatory systems to deliver oxybutynin to the bladder, the site of its activity in treating urinary incontinence. Set forth herein is a new and useful device and method for locally delivering and controllably releasing a therapeutically effective amount of oxybutynin ranging from 0.5 to 5.0 mg/day for up to twenty-eight contiguous days. In particular, a device of the instant invention is based upon the discovery that surprisingly and unexpectedly, trifluoropropylmethyl/dimethyl siloxane elastomer controls the release of oxybutynin, and thus can be used to controllably release oxybutynin. Particular methods of producing rings having applications in a device or method of the present invention are set forth infra.

Example 1

Preparation of a Two-bore, Trifluoropropylmethyl/ dimethyl Siloxane Elastomer Ring as Schematically Shown in FIG. 1A 40 g part A and 40 g part B trifluoropropylmethyl/ dimethyl siloxane elastomer formation (NuSil Technology, CF2-3521 grade) were weighed into a 100 g capacity Hauschild mixing cup and subsequently mixed for 10 seconds in a Hauschild Model 501 T speed mixer. A metal spatula was then used to scrape down the sides of the mixing cup and further blend the two starting components. A final 14-second speed mixer cycle was supplied to ensure blend uniformity.

Both halves of an insert mold with key bore and insert dimensions as follows were lightly coated in an ethanol/ water solution of DARVAN WAQ (R.T. Vanderbilt Co.) and allowed to air dry; outer diameter=5.5±0.1 cm, cross-section diameter=8.5±0.5 mm, insert bore length=2.2±0.1 cm, insert bore diameter=3.2±0.1 cm. Between 12–15 grams of the 1:1 part A:part B blend were manually placed via metal spatula into the pin containing half of the mold. The insert pins were positioned in the filled portion of the mold and matched unfilled mold half was mated into place.

The filled mold assembly was then compressed between the unheated platens of a Kuntz injection molding machine in order to discharge excess polymer blend from the mold. During this compression step, the insert pins were manually held in place to avoid ejection by the applied air pressure. The discharged blend material was removed from the outside of the mold assembly and discarded.

The compressed, filled mold assembly was then placed between the preheated platens of a model 3912 Carver press. A pressure of 5,000 psi was applied and heating of the assembly for 15 minutes at 150° C. was performed to affect elastomer cure. During approximately the first 5 minutes of this curing step, the insert pins were physically held in place to avoid ejection from the mold.

After 15 minutes at 150° C., the mold was removed from the Carver press and cooled on the Kuntz machine's chiller for a sufficient time to allow easy separation of the mold halves and facilitate manual handling. The cured ring was separated from the mold by hand. The insert pins were then carefully removed from the molded part by gently pulling them out without tearing or otherwise deforming the insert bore.

Example 2

Preparation of an Insert Segment as Schematically Shown in FIG. 1B

Insert segments of the following dimensions were prepared from molded insert rings prepared as discussed in Example 1 above, by cutting out the insert bore portion of an insert ring with a sharp instrument: length=3.5±0.1 cm, cross sectional diameter=8.5±0.5 mm. Such segments are schmatically shown in FIG. 1B.

Example 3

Preparation of a Trifluoropropylmethyl/dimethyl Siloxane Elastomer Insert Rings Containing One Oxybutynin Filled Bore Using a syringe, one bore of a ring produced pursuant to Example 1 above, was completely filled with a 200:1 blend of R2602:CAT-02 (both from NuSil Technology) condensation cure silicone sealant. The insert ring's other bore was partially (about 3 mm) filled with this sealant. The sealant was allowed to cure for 5 minutes.

96 grams of PLY-7610 (NuSil Technology) and 4 grams of CAT-01 (NuSil Technology) were weighed into a 40 gram capacity Hauschild mixing cup. Three 26 second spin cycles in a Hauschild model AM 501 T speed mixer were conducted to blend these materials. The resulting blend was labeled CAT-22 (and is hereinafter referenced as such).

1 gram CAT-22, 8 grams of R2602 and 13.5 grams of oxybutynin base were mixed for 26 seconds in the Hauschild model AM 501 T speed mixer. A sufficient amount of the resulting paste was injected via syringe into a partially filled insert ring bore to give a 1–1.5 cm long drug containing section. After its addition, the paste was compacted with a small glass stirring rod so it contacted the initially injected 200:1 R2602:CAT-02 silicone sealant layer. The remainder of this insert bore was finally filled with a layer of the 200:1 R2602-02 sealant. The ring was given 24 hours at ambient conditions to allow the bore sealants to fully cure. By calculation, based on weights before and after additions, about 18 mg of oxybutynin were present in the ring.

Example 4

Preparation of Trifluoropropylmethyl/dimethyl Siloxane Elastomer Insert Segments Containing Oxybutynin 16 grams of R2602 (NuSil Technology) and 2 grams of previously described CAT-22 were weighed into a 40 gram capacity Hauschild mixing cup. Two 16 second spin cycles in a Hauschild model AM 501 T speed mixer were conducted to blend these materials.

Using a syringe fitted with an 18 gauge needle, the bore of a trifluoropropylmethyl/dimethyl siloxane elastomer insert segment, from Example 2 above, was filled to one third volume with the 8:1 R2602:CAT-22 condensation cure silicone sealant. The sealant was allowed to cure for 24 hours.

2 grams of R2602, 0.25 grams of CAT-22 and 3.4 grams of oxybutynin base were weighed into a 40 gram capacity Hauschild mixing cup. Two 16 second spin cycles in a Hauschild model AM 501 T speed mixer were performed to blend these materials. About 30 mg of this paste was injected, via syringe, into the insert segment's bore and subsequently compacted so that it contacted the initially injected 8:1 R2602:CAT-22 condensation cure silicone sealant layer. The remainder of the bore was then filled with 8:1 R2602:CAT-22 sealant. Cure of the bore's contents was achieved at ambient conditions overnight. By calculation, based weights before and after additions, about 18 mg of oxybutynin were present in the segment.

Example 5

In Vitro Drug Release Testing of Ring Segments

Figure 2:
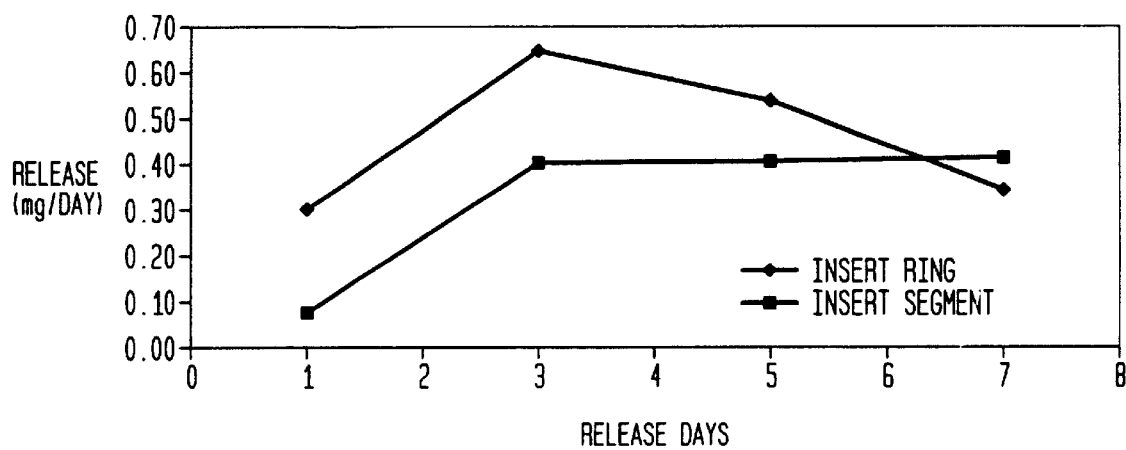
FIG. 2 is a graph of the comparison of the release profiles between an oxybutynin insert Ring and an insert segment.

Seven day in vitro oxybutynin release profiles were generated from rings and segments produced pursuant to Examples 3 and 4. The datapoints for both ring and segment devices in FIG. 2 represent the average of three samples per type.

In vitro testing of rings produced pursuant to Example 3 was performed by immersing individual rings in 300 ml of 0.05 M, pH 6.5 Sodium Dodecyl Sulfate (SDS) solution within 500 ml capacity "NALGENE" screw cap bottles. The plastic containers were shaken at about 140 RPM in a 37° C. water bath. Aliquots of receptor media were withdrawn at 1, 3, 5 and 7 days and individually analyzed by reverse phase HPLC. For the HPLC analyses, a $C_8$, 5 micron, 4.6×150 mm Kromasil column was employed. The buffer was 32:68 mixture of acetonitrile: (0.01 M $KH_2PO_4$, 0.05 M Dimethyl Octyl Amine (DMOA), with pH=2). The average amount of drug released at each Potassium Phosphate Monobasic timepoint was plotted vs. time, as indicated in FIGS. 2–5.

In vitro testing of segments from such rings was conducted in a 500 ml capacity DISTEK USP dissolution baths at 37° C. Individual segments were suspended in basket holder and immersed in 500 ml of 6.5 pH. 0.05 M SDS solution. The basket holders were rotated at 100 rpm. Aliquots of receptor media were withdrawn at 1, 3, 5 and 7 days and individually analyzed by reverse phase HPLC. The HPLC conditions were the same as described in the previous paragraph. The average amount of drug released at each timepoint was plotted versus time. As shown in FIGS. 2–5 oxybutynin can be released from trifluoropropylmethyl/dimethyl siloxane elastomer in a controlled manner.

Example 6

Preparation of Trifluoropropylmethyl/dimethyl Siloxane Elastomer Insert Segments Containing Sufficient Oxybutynin to Deliver About 0.5 mg/day in vitro Over 7 Days 8 grams of R2602 (NuSil Technology) and 1 gram of previously described CAT-22 were weighed into a 40 gram capacity Hauschild mixing cup. A 22 second spin cyclein in a Hauschild model AM 501 T was performed to blend these materials.

Using a syringe fitted with an 18 gauge needle, the bore of a trifluoropropylmethyl/dimethyl silicone elastomer insert segment, from Example 3, was filled with the 8:1 R2602:CAT-22 condensation cured silicone sealant to about $\frac{1}{8}^{th}$ of its length.

8 grams of R2602, 1 gram of CAT-22 and 13.5 grams of oxybutynin base were weighed into a 40 gram capacity Hauschild mixing cup. Two 16 second spin cycles in a Hauschild model AM 501 T speed mixer was performed to blend these materials. About 50 mg of the resulting paste was injected, via syringe, into the insert segment's bore. This amount of drug containing paste filled about ¾ of the bore's length. The remainder of the bore was then filled with 8:1 R2602:CAT-22 sealant. Cure of the bore's contents was achieved at ambient conditions over the course of 48 hours. By calculation, based on weights before and after additions, about 32 mg of oxybutynin were present in the segment.

Example 7

Figure 3:
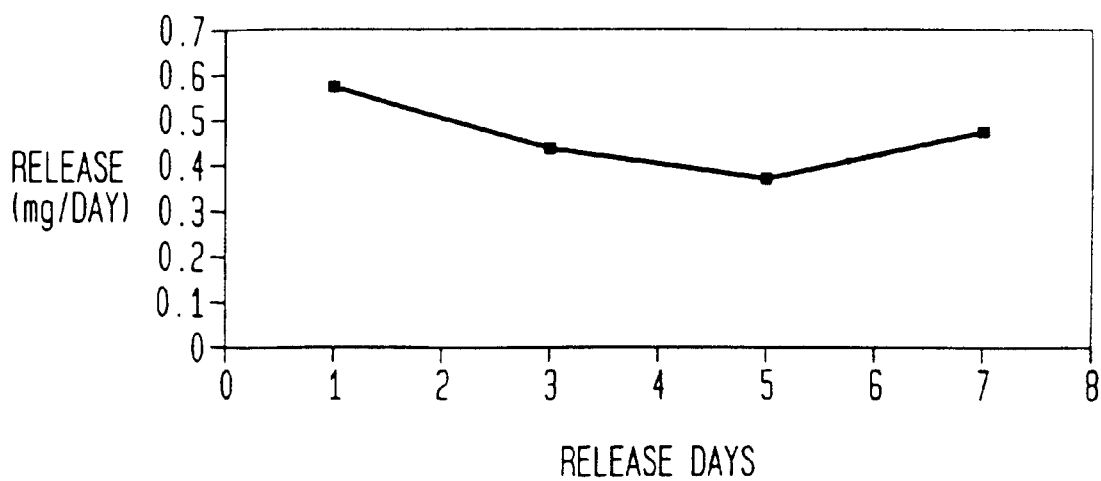
FIG. 3 is a graph of the drug release profile data from trifluoropropylmethyl/dimethyl siloxane elastomer segments that deliver about 0.5 mg/day of oxybutynin.
Figure 4:
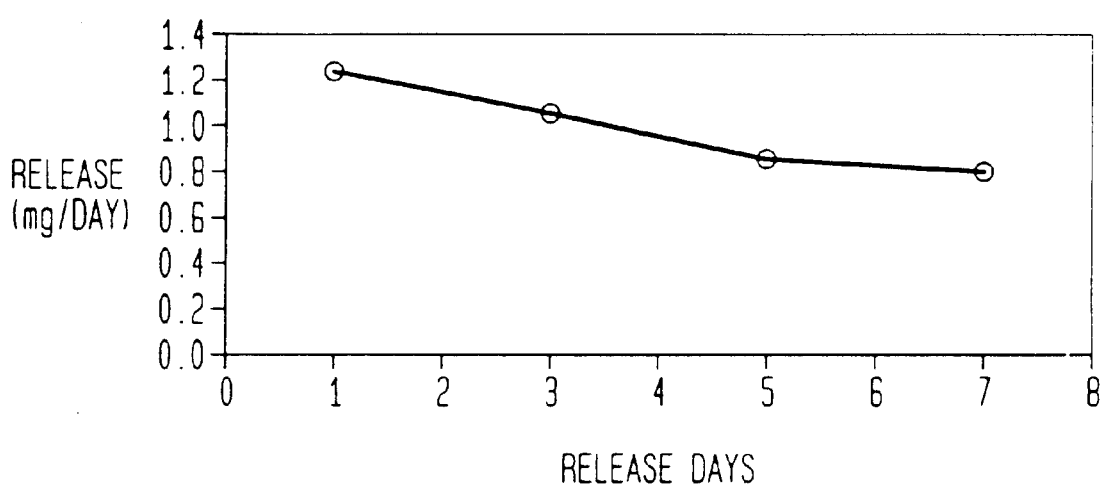
FIG. 4 is a graph of the drug release profile data from trifluoropropylmethyl/dimethyl siloxane elastomer segments that deliver about 1.0 mg/day of oxybutynin.
Figure 5:
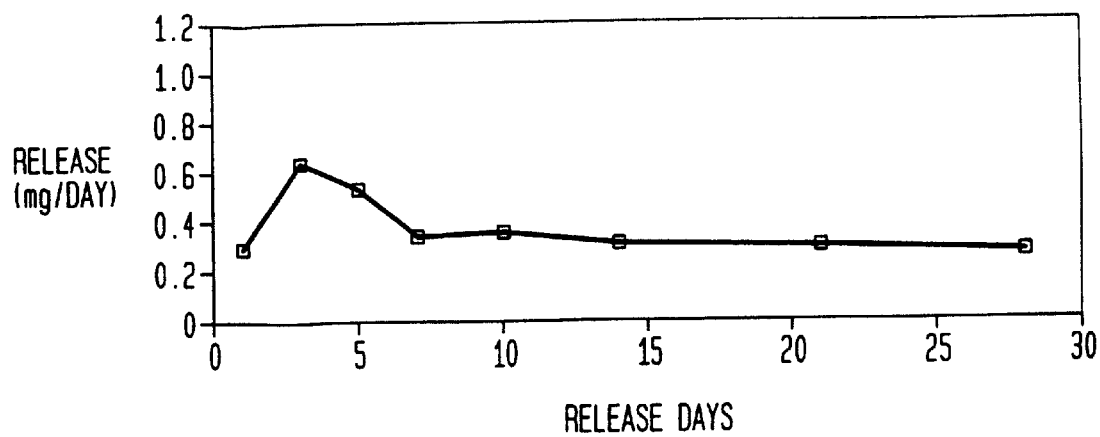
FIG. 5 is a graph of the drug release profile data from trifluoropropylmethyl/dimethyl siloxane elastomer rings that deliver about 0.5 mg/day of oxybutynin over 28 contiguous days.

In vitro Drug Release Testing of Segments of Rings Comprising Trifluoropropylmethyl/dimethyl Siloxane Elastomer Insert Segments Containing Sufficient Oxybutynin to Deliver About 0.5 mg/day in vitro Over 7 Days Seven day in vitro oxybutynin release profiles were generated from segments of rings described in Example 6 above. The datapoints for segments of rings comprising trifluoropropylmethyl/dimethyl siloxane elastomer insert segments containing sufficient oxybutynin to deliver about 0.5 mg/day in vitro over 7 days in FIG. 3 represent an average of three samples.

In vitro testing of these segments of rings was conducted in 500 ml capacity "DISTEK USP" dissolution baths at 37° C. Individual segments were suspended in basket holders and immersed in 500 ml of 6.5 pH. 0.05 M SDS solution. The basket holders were rotated at 100 rpm. Aliquots of receptor media were withdrawn at 1, 3, 5 and 7 days and individually analyzed by reverse phase HPLC. For the HPLC analyses, a $C_8$, 5 micron, 4.6×150 mm Kromasil column was employed. The buffer was 32:68 mixture of acetonitrile: (0.01 M $KH_2PO_4$, 0.05 M DMOA, with pH=2).

The average drug released from these segments was plotted versus time and compared to the release data generated for previously described ring segments. This comparison is presented in FIG. 3. The data in FIG. 3 show that the segments of such rings released on average, close to 0.5 mg of oxybutynin per day. FIG. 3 also demonstrates that oxybutynin can be released from trifluoropropylmethyl/dimethyl siloxane elastomer in a controlled manner.

Example 8

Preparation of Trifluoropropylmethyl/dimethyl Siloxane Elastomer Insert Segments Designed to Deliver Oxybutynin at a Rate of 1.0 m/day Over 7 Days 8 grams of R2602 (NuSil Technology) and 1 gram of previously described CAT-22 were mixed as described above.

2 grams of R2602, 0.25 gram of CAT-22 and 3.38 grams of oxybutynin base were weighed into a 40 gram capacity Hauschild mixing cup. Two 16 second spin cycles in a Hauschild model AM 501 T speed mixer was performed to blend these materials. Using a cuvette stirrer, about 125 mg of the resulting paste was compacted into the middle of the bore of an Example 1 trifluoropropylmethyl/dimethyl siloxane elastomer insert segment. The top and bottom portions of the bore were then filled with a very small amount of 8:1 R2602:CAT-22 sealant, applied via syringe. Cure of the bore's contents was achieved at ambient conditions over the course of 24 hours. By calculation, based on weights before and after each addition to the bore, about 75 mg of oxybutynin were present in the segment.

Example 9

Preparation of Trifluoropropylmethyl/dimethyl Siloxane Elastomer Insert Segments Containing Sufficient Oxybutynin to Deliver Between 1.0 and 1.5 mg/day in vitro Over 7 Days 8 grams of R2602 (NuSil Technology and 1 gram of previously described CAT-22 were weighed into a 40 gram capacity Hauschild mixing cup. Two 16 second spin cycles in a Hauschild model AM 501 T speed mixer were performed to blend these materials.

8 grams of R2602, 1 gram of CAT-22 and 4.8 grams of oxybutynin base were weighed into a 40 gram capacity Hauschild mixing cup. Two 16 second spin cycles in a Hauschild model AM 501 T speed mixer were performed to blend these materials. About 191 mg of the resulting paste was injected, via syringe, into the bore of trifluoropropylmethyl/dimethyl siloxane elastomer insert segment, described above. The top portion of the bore was then filled with a very small amount of 8:1 R2602:CAT-22 sealant, applied via syringe. Cure of the bore's contents was achieved at ambient conditions over the course of 48 hours. By calculation, based on weights before and after additions, about 67 mg of oxybutynin were present in the segment.

Example 10

Preparation of Trifluoropropylmethyl/dimethyl Siloxane Elastomer Insert Segments Containing Sufficient Oxybutynin to Deliver Between 1.5 and 2.0 mg/day in vitro Over 7 Days 8 grams of R2602 (NuSil Technology) and 1 gram of previously described CAT-22 were mixed as described above.

8 grams of R2602, 1 gram of CAT-22 and 9 grams of oxybutynin base were weighed into a 40 gram capacity Hauschild mixing cup. Two 16 second spin cycles in a Hauschild model AM 501 T speed mixer were performed to blend these materials. About 240 mg of the resulting paste was injected, via syringe, into the bore of a trifluoropropylmethyl/dimethyl siloxane elastomer insert segment, from Example 2. The amount of drug and containing paste filled nearly the entire bore. The top portion of the bore was then filled with a very small amount of the 8:1 R2602:CAT-22 sealant, applied via syringe. Cure of the bore's contents was achieved at ambient conditions overnight. By calculation, based on weights before and after additions, about 120 mg of oxybutynin was present in the segment.

Example 11

Preparation of a Single Bore Insert Ring Comprised of Separate, Continuous PDMS and Trifluoropropylmethyl/dimethyl Siloxane Elastomer Sections 30 grams part A and 30 grams of part B trifluoropropylmethyl/dimethyl siloxane elastomer formulation (NuSil Technology, CF2-3521 grade) were weighed into a 100 gram capacity Hauschild mixing cup and subsequently mixed for 16 seconds in a Hauschild model AM 501 T speed mixer. A metal spatula was then used to scrape down the sides of the mixing cup and further blend the two starting components. A final 16-second speed mixer cycle was applied to ensure blend uniformity.

Continuous sections of matching halves of the insert mold from Example 2 were manually filled with the uncured trifluoropropylmethyl/dimethyl siloxane elastomer mix such that one of the pin insert portions of the mold contained this material. Approximately 50% of the mold's volume was filled in this manner. An insert pin was then positioned in the partially filled mold.

30 grams part A and 3.0 grams of part B dimethyl siloxane elastomer formulation (NuSil Technology, MED-4210 grade) were weighed into a 100 gram capacity Hauschild mixing cup and subsequently mixed for two 16 second cycles in a Hauschild model AM 501 T speed mixer. The unfilled matching halves of the partially filled mold described above were manually filled with this uncured dimethyl siloxane mix. No insert pin was positioned in this section of the mold, however.

The entire mold was next assembled, placed between the unheated platens of a model 3912 Carver press, and compressed to 5,000 psi in order to discharge excess polymer blend from the mold. The excess material was removed from the outside of the mold assembly and discarded. The filled mold was then transferred to the pre-heated (150° C.) platens of a model 284-1 Kuntz injection molding machine and held there for 15 minutes to affect cure. The mold was cooled to room temperature and disassembled. Careful manual removal of the lone insert pin yielded the single bore insert ring comprised of separate, continuous PDMS and trifluoropropylmethyl/dimethyl siloxane elastomer sections that is depicted in FIG. 6A.

Example 12

Figure 6B:
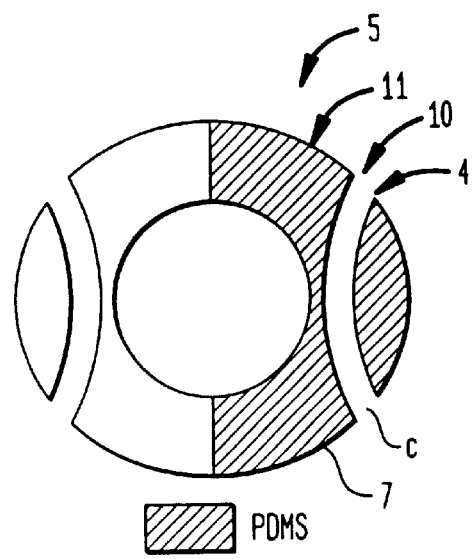
FIG. 6B is a schematical cross sectional view of a ring of a device of the invention comprising one portion trifluoropropylmethyl/dimethyl siloxane elastomer, and one portion polydimethylsiloxane, wherein the bore comprises a first bore located in the trifluoropropylmethyl/dimethyl siloxane elastomer portion, and a second bore located in the polydimethylsiloxane portion.

Preparation of a Two Bore Ring Comprised of Separate, Continuous PDMS and Trifluoropropylmethyl/dimethyl Siloxane Elastomer Sections (Corresponds to FIG. 6B)

The two bore insert ring schematically shown in FIG. 1 was prepared using nearly the same procedure described in immediately above, the only difference being that an additional insert pin was positioned in the uncured dimethyl siloxane mix filled portion of the mold prior to curing on the Kuntz machine.

Rings Comprising at Least Two Shields into which Oxybutynin is Insoluble

Another design of a ring having applications herein comprises two portions and at least two shields located between the portions, wherein oxybutynin is substantially insoluble in the at least two shields. The shields prevent contact between the two portions, and thus prevent migration of the oxybutynin into the ring. Based on the segment release data, and the comparison of the release from rings vs. segments, it was determined minimal diffusion of oxybutynin into the ring may occur when a pharmaceutical composition comprising oxybutynin and tin catalyzed silicone polymer excipient was placed into an at least one bore in the TFP portion of the ring. To limit such diffusion, at least two shields comprising polytetrafluoroethylene or a barium sulfate composite were placed in the rings between a first portion comprising trifluoropropylmethyl/dimethyl siloxane elastomer having at least one bore and a second portion. Since oxybutynin is substantially insoluble in polytetrafluoroethylene and a barium sulfate composite, these shields prohibit the diffusion of oxybutynin from the trifluoropropylmethyl/dimethyl siloxane elastomer portion to other parts of the ring. As a result, a substantial portion of the oxybutynin initially placed in the at least one bore is controllably released and locally delivered to the cervical region, and thus is available to treat the female's urinary incontinence. Rings having only one trifluoropropylmethyl/dimethyl siloxane elastomer portion with at least one bore therein use only two shields. Similarly, rings comprising two trifluoropropylmethyl/dimethyl siloxane elastomer portions having at least one bore utilize four shields. To prepare the rings, PTFE disks, cut to the about 8 mm in diameter, were placed in a mold at 90° angles. At least one pin was then set in the mold and fixed in place. The pin would be located in a portion of the mold that was between two shields. FIGS. 7A and 7B schematically show the location of such shields in a ring of a device of the invention. After placement of the shields and the pin(s), trifluoropropylmethyl/dimethyl siloxane elastomer was poured into the mold. Then, the mold was sealed and heated to cure the polymer. Particular methods of producing such rings is set forth infra.

Example 13

Preparation of a Two Bore Insert Ring Comprised of Separate, Continuous PDMS Sections and Trifluoropropylmethyl/dimethyl Siloxane Elastomer, and Containing Four Drug Impermeable PTFE Shields Between These Sections 30 grams part A and 30 grams part B of trifluoropropylmethyl/dimethyl siloxane elastomer formulation (NuSil Technology, CF2-3521 grade) were weighed into a 100 gram capacity Hauschild mixing cup and subsequently mixed for 16 seconds in a Hauschild model AM 501 T speed mixer. A metal spatula was then used to scrape down the sides of the mixing cup and further blend the two starting components. A final 16-second speed mixer cycle was applied to ensure blend uniformity.

Continuous sections of matching halves of the insert mold from Example 2 were manually filled with the uncured trifluoropropylmethyl/dimethyl siloxane elastomer mix such that one of the pin insert portions of the mold contained this material. Approximately 50% of the mold's volume was filled in this manner. An insert pin was then positioned in the partially filled mold. Two 8 mm diameter, 2 mm thick PTFE disks were manually situated in an upright position within the uncured polymer mix several millimeters from both the distal and proximal ends of the insert pin.

30 grams part A, 3 gram part B of dimethyl siloxane elastomer formulation (NuSil Technology, MED-4210 grade) were weighed into a 100 gram capacity Hauschild mixing cup and subsequently mixed for two 16 second cycles in a Hauschild model AM 501 T speed mixer. The unfilled matching halves of the partially filled mold described above were manually filled with this uncured dimethyl siloxane mix. An insert pin was then positioned in this section of the mold. Two 8 mm diameter, 2 mm thick PTFE disks were manually placed in a perpendicular manner within the uncured polymer mix several millimeters from both the distal and proximal ends of the insert pin.

The entire mold was next carefully assembled, placed between the unheated platens of a model 3912 Carver press and compressed at 5000 psi in order to discharge excess polymer blend from the mold. The excess material was removed from the outside of the mold assembly and discarded. The filled mold was then transferred to the preheated (150° C.) platens of a model 284-1 Kuntz injection molding machine and held there for 15 minutes to affect cure. The mold was cooled to room temperature and disassembled. Careful manual removal of the insert pins yielded the two bore insert ring comprised of separate, continuous PDS and trifluoropropylmethyl/dimethyl siloxane elastomer sections and containing four drug impermeable PTFE barriers between these sections that is shown in FIG. 7B.

Example 14

Preparation of a Single Bore Insert Ring Comprising Separate, Continuous PDMS and Trifluoropropylmethyl/dimethyl Siloxane Elastomer Sections, and Two Drug Impermeable PTFE Barriers Between These Sections 30 grams part A and 30 grams part B of trifluoropropylmethyl/dimethyl siloxane elastomer formulation (NuSil Technology, CF2-3521 grade) were weighed into a 100 gram capacity Hauschild mixing cup and subsequently mixed for 16 seconds in a Hauschild model AM 501 T speed mixer. A metal spatula was then used to scrape down the sides of the mixing cup and further blend the two starting components. A final 16-second speed mixer cycle was applied to ensure blend uniformity.

Continuous sections of matching halves of the insert mold from Example 2 were manually filled with the uncured trifluoropropylmethyl/dimethyl siloxane elastomer mix such that one of the pin insert portions of the mold contained this material. Approximately 50% of the mold's volume was filled in this manner. An insert pin was then positioned in the partially filled mold. Two 8 mm diameter, 2 mm thick PTFE disks were manually situated in an upright position within the uncured polymer mix several millimeters from both the distal and proximal ends of the insert pin.

30 grams part A, 3 grams part B of dimethyl siloxane elastomer formulation (NuSil Technology, MED-4210 grade) were weighed into a 100 gram capacity Hauschild mixing cup and subsequently mixed for two 16 second cycles in a Hauschild model AM 501 T speed mixer. The unfilled matching halves of the partially filled mold described above were manually filled with this uncured dimethyl siloxane mix. However, no insert pin was positioned in this section of the mold, however.

The entire mold was next carefully assembled, placed between the unheated platens of a model 3912 Carver press and compressed at 5000 psi in order to discharge excess polymer blend from the mold. The excess material was removed from the outside of the mold assembly and discarded. The filled mold was then transferred to the preheated (150° C.) platens of a model 284-1 Kuntz injection molding machine and held there for 15 minutes to affect cure. The mold was cooled to room temperature and disassembled. Careful manual removal of the insert pin yielded the single bore insert ring comprised of separate, continuous PDMS and trifluoropropylmethyl/dimethyl siloxane elastomer sections and containing two drug impermeable PTFE barriers between these sections, such as schematically shown in FIG. 7.

Rings with at Least Two Barium Sulfate Composite Shields

Another ring having applications herein comprises two portions and at least two oxybutynin impermeable barium sulfate (BaSO$_4$) composite shields located between the two portions. These shields prevent contact between the two portions and diffusion of oxybutynin to other portions of the ring. Barium sulfate composites have been used on numerous occasions to control the release of various drugs through silicone.

BaSO$_4$ composite shields have ready applications in rings wherein the portion comprising the at least one bore comprises trifluoropropylmethyl/dimethyl siloxane elastomer. Such shields can also be readily used in rings comprising a combination of materials, e.g., rings comprising TFP and PDMS. Examples of such rings are schematically shown in FIGS. 7 and 8. Particular methods of making such rings, which are schematically shown in FIGS. 7–8 are set forth below:

Example 15

Preparation of a Single Bore Insert Ring Comprised of Separate, Continuous PDMS and Trifluoropropylmethyl/dimethyl Siloxane Elastomer Sections Separated by Two Drug Impermeable Barium Sulfate Composite Regions 30 grams part A and 30 grams part B of trifluoropropylmethyl/dimethyl siloxane elastomer formulation (NuSil Technology, CF2-3521 grade) were weighed into a 100 gram capacity Hauschild mixing cup and subsequently mixed for 16 seconds in a Hauschild model AM 501 T speed mixer. A metal spatula was then used to scrape down the sides of the mixing cup and further blend the two starting components. A final 16-second speed mixer cycle was applied to ensure blend uniformity.

Continuous sections of matching halves of the insert mold from Example 2 were manually filled with the uncured trifluoropropylmethyl/dimethyl siloxane elastomer mix such that one of the pin insert portions of the mold contained this material. Approximately 40% of the mold's volume was filled in this manner. An insert pin was then positioned in this portion of the mold.

10 grams part A, 1 gram part B of dimethyl siloxane elastomer formulation (NuSil Technology, MED-4210 grade) and 10.2 grams of BaSO4 were weighed into a 40 gram capacity Hauschild mixing cup and subsequently mixed for one 16-second cycle in a Hauschild model AM 501 T speed mixer. A metal spatula was then used to scrape down the sides of the mixing cup and further blend the two starting components. A final 16-second speed mixer cycle was applied. Sufficient amounts of this barrier mix were manually placed in the mold adjacent to both ends of the uncured trifluoropropylmethyl/dimethyl siloxane elastomer section such that an unfilled gap of about 1.5 mm was created between each BaSO$_4$ barrier and the uncured trifluoropropylmethyl/dimethyl siloxane elastomer section. These gaps insured formation of distinct, but continuous sections upon subsequent compression and cure. The length of both BaSO$_4$ barrier areas was roughly 1 cm.

50 grams part A, 5 grams part B of dimethyl siloxane elastomer formulation ( NuSil Technology, MED-4210 grade) were weighed into a 100 gram capacity Hauschild mixing cup and subsequently mixed for two 16 second cycles in a Hauschild model AM 501 T speed mixer. The remaining unfilled matching halves of the partially filled mold described above were manually filled with this uncured dimethyl siloxane mix. In the mold, this blend was allowed to contact the two BaSO$_4$ barrier areas so that there were no gaps between this component's area and the two BaSO$_4$ barrier areas. No insert pin was positioned in this section of the mold.

The entire mold was next carefully assembled, transferred to the pre-heated (150° C.) platens of a model 284-1 Kuntz injection molding machine and held there for 18 minutes to affect cure. The mold was cooled to room temperature and disassembled. Careful manual removal of the lone insert pin yielded the single bore insert ring comprised of continuous PDMS and trifluoropropylmethyl/dimethyl siloxane elastomer sections that were separated by two BaSO4 composite sections, as schematically shown in FIG. 8B.

Example 16

Half-TFP, Half-Barium Sulfate Composite Rings 30 grams part A and 30 grams part B of trifluoropropylmethyl/dimethyl siloxane elastomer formulation (NuSil Technology, CF2-3521 grade) were weighed into a 100 gram capacity Hauschild mixing cup and subsequently mixed for 16 seconds in a Hauschild model AM 501 T speed mixer. A metal spatula was then used to scrape down the sides of the mixing cup and further blend the two starting components. A final 16-second speed mixer cycle was applied to ensure blend uniformity.

Continuous sections of matching halves of the insert mold from Example 2 were manually filled with the uncured trifluoropropylmethyl/dimethyl siloxane elastomer mix such that one of the pin insert portions of the mold contained this material. Approximately 40% of the mold's volume was filled in this manner. An insert pin was then positioned in this portion of the mold.

10 grams part A, 1 gram part B of dimethyl siloxane elastomer formulation ( NuSil Technology, MED-4210 grade) and 10.2 grams of BaSO4 were weighed into a 40 gram capacity Hauschild mixing cup and subsequently mixed for one 16-second cycle in a Hauschild model AM 501 T speed mixer. A metal spatula was then used to scrape down the sides of the mixing cup and further blend the two starting components. A final 16-second speed mixer cycle was applied. The unfilled matching halves of the partially filled mold described above were manually filled with this uncured dimethyl siloxane/barium sulfate composite. No insert pin was positioned in this section of the mold, however.

The entire mold was next carefully assembled, transferred to the preheated (150° C.) platens of a model 284-1 Kuntz injection molding machine and held there for 18 minutes to affect cure. The mold was cooled to room temperature and disassembled. Careful manual removale of the lone insert pin yielded the single bore insert ring comprised of separate, continuous trifluoropropylmethyl/dimethyl siloxane elastomer and PDMS/barium sulfate composite sections, as shown in FIG. 9.

Example 17

Formation of Pharmaceutical Composition for Insertion into a Bore of a Ring

As explained above, a device of the invention can locally deliver, and controllably release from about 0.5 mg/day to about 5.0 mg/day of oxybutynin for up to twenty-eight days, or as needed. Preferred dosages are about 0.5 mg/day, about 1.0 mg/day and about 5.0 mg/day for up to twenty-eight days. All three dosages make use of a pharmaceutical composition comprising about 60% by weight oxybutynin and about 40% by weight silicone excipient. To determine the dosage for a particular duration, the amount of pharmaceutical composition placed into the bores of the rings was varied. For example, to make a 0.5 mg/day ring or segment, approximately 55–57 mg of pharmaceutical composition was added to the insert. This 55–57 mg of pharmaceutical composition results in approximately 32–35 mg oxybutynin available for local delivery.

Similarly, to prepare a 1.0 mg/day ring or segment thereof, approximately 120–125 mg of the pharmaceutical composition is required to make about 72–75 mg oxybutynin available for local delivery. This amount of pharmaceutical composition fills about ¾ of the volume of a bore in the ring, wherein the bore has a diameter of about 3.2 mm, and a length of about 1.65 cm. In order for a ring or segment thereof to locally deliver and controllably release about 5.0 mg/day of oxybutynin, approximately 200–205 mg of pharmaceutical composition is required. This amount of pharmaceutical composition results in 120–123 mg oxybutynin available for delivery, and uses the entire volume of the bore.

As explained above, the required amounts of pharmaceutical composition in the bore to deliver a particular amount of oxybutynin is known, the volume of the bore the each particular amount of pharmaceutical composition occupies is known, and the concentration of oxybutynin in the pharmaceutical composition is known. With this information, rods of the pharmaceutical composition can be produced, and the amount of oxybutynin in a particular length of rod can be readily determined. As a result, once the rods are formed, a medical provider administering a device of the invention can merely cut a portion of the rod which has the correct amount of pharmaceutical composition, and insert that portion into the bore of the ring.

Figure 10E:
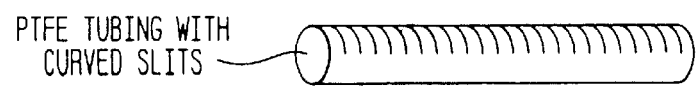
FIG. 10E shows a side view of polytetrafluoroethylene tubing with exemplary slits perpendicular to the tubing which may be used in the present invention to form pharmaceuticla composition rods.

Numerous methods readily available to the skilled artisan can be used to form rods of a pharmaceutical composition comprising oxybutynin and an excipient. A particular method involves using polytetrafluoroethylene (PTFE) tubing having an inner diameter of 3.2 mm. Initially, slits are made in the PTFE tubing. These slits can be either parallel to the tubing, as schematically set forth in FIG. 10D, or perpendicular to the tubing, as schematically shown in FIG. 10E. Then, a pharmaceutical composition comprising about 60% by weight oxybutynin, and about 40% by weight tin catalyzed silicone polymer excipient is placed in the tubing. The tube's contents are then permitted to cure for about 24 hours at room temperature.

Once cured, the PTFE tubing is peeled off, leaving a rod of the pharmaceutical composition. The rods can be cut to a size which corresponds to the dosage to be delivered, and inserted into the bore of the ring. These rods can be prepared days, weeks or even months prior to their actual use.

Example 18

Animal Studies

The urinary bladder is a smooth muscle organ whose function is to collect and store urine at low intravesical pressure; then, periodically, to expel the urine via a highly coordinated sustained contraction through a relaxed urethra. Efficient emptying requires contraction of the bladder body smooth muscle elements coordinated with relaxation of the bladder neck and urethra (A, B). Continence, especially in women, depends upon the maintenance of tonic tension within the urethra and a stable detrusor muscle (C, D). Increases in bladder pressure such as those that occur in unstable bladders or hyperreflexia can result in incontinence (C, D).

Pharmacologically, the bladder can be separated into two parts, body and base. Both, responses to autonomic agonists and receptor distribution characterize this division (E). Muscarinic receptor density and contractile responses to cholinergic stimulation are greatest in the bladder body and weakest in the base. Similarly, α-adrenergic receptor density and relaxant response to stimulation are greatest in the body and weakest in the base; whereas—adrenergic receptor density and contractile responses to stimulation are greatest in the base and weakest in the body (E). Both unstable bladder contractions and hyperreflexia are mediated by cholinergic mechanisms, and thus the administration of agents that can both, relax the bladder and inhibit these cholinergic spikes would be of therapeutic benefit in the treatment of incontinence (C, D).

One agent that has proven to be clinically effective in the treatment of incontinence is oxybutynin (6–9). Oxybutynin relaxes the bladder by muscarinic inhibition and by direct relaxation of smooth muscle. Although the therapeutic effects of oxybutynin make it the most useful drug for inhibition of unstable bladder and bladder relaxation for more than 20 years [1,2], the side effects associated with oral medication can be uncomfortable and significantly influence the patients compliance. Oxybutynin has a short half-life and a low systemic bioavailability after oral administration because of extensive first-pass metabolism, which also causes typical plasma concentration—time profile peaks and troughs. The duration of symptom relief often is not satisfying. This combination of side-effects under peak plasma concentrations and short symptom relief can cause the discontinuance of treatment The development of a vaginal system for continuous medication would be of great value in producing a prolonged and continuous therapeutic blood level. It could allow a much longer application-free interval and improve the patients convenience and compliance. Additionally, the constant release would prevent the peaks and troughs of oral medication, and reduce the level and intensity of side effects, which can be directly related to the high plasma levels obtained immediately after taking the oral medication.

Methods 12 rabbits were separated into 4 groups of 3 rabbits each. Under pentobarbital anesthesia (25 mg/kg, iv) A cylinder-shaped, curved silastic insert was placed in the vagina of each rabbit. This was accomplished by the following: a midline laparotomy was performed and after transvaginal insertion the implant was anchored with a single 2.0 silk suture through the outer vaginal wall and knotted to a 1 cm section of a medical-grade tubing to avoid damage to the vaginal wall. The inserts in group one contained vehicle, the inserts in groups 2–4 were calculated to release oxybutynin at rates of 0.5 mg/day; 1 mg/day; and 5 mg/day respectively. The inserts remained in place for 7 days. Samples of blood (2 ml) were collected at 12:00 noon on days 1, 3, 5 and 7. After the last blood sample was obtained, each rabbit was sedated and cystometries were performed. Immediately after the cystometry, the rabbit was euthanized, the lower urinary tract including the vagina was removed and evaluated for irritation. In addition, the bladder was excised and weighed.

The samples of blood were frozen and subsequently analyzed. The oxybutynin and desethyloxybutynin concentrations were quantified.

Results

Figure 11:
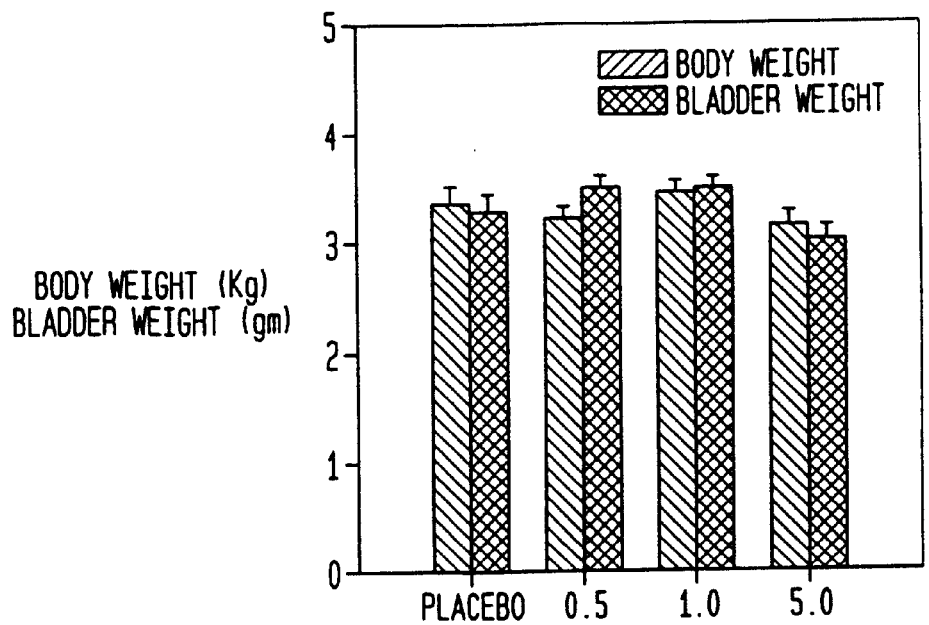
FIG. 11: Effect of the Oxybutynin implants on the rabbit and bladder weight. Each bar is the mean SEM of 3 individual rabbits.
Figure 12:
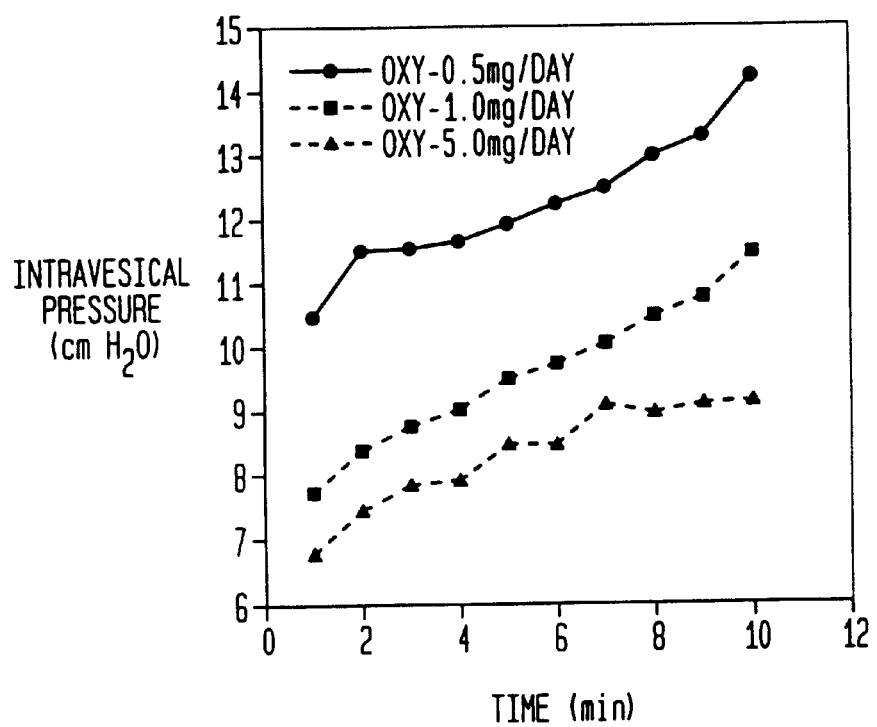
FIG. 12: Effect of different oxybutynin-doses on cystometric pressures. Each point is the mean of cystometric curves performed on three individual rabbits.
Figure 13:
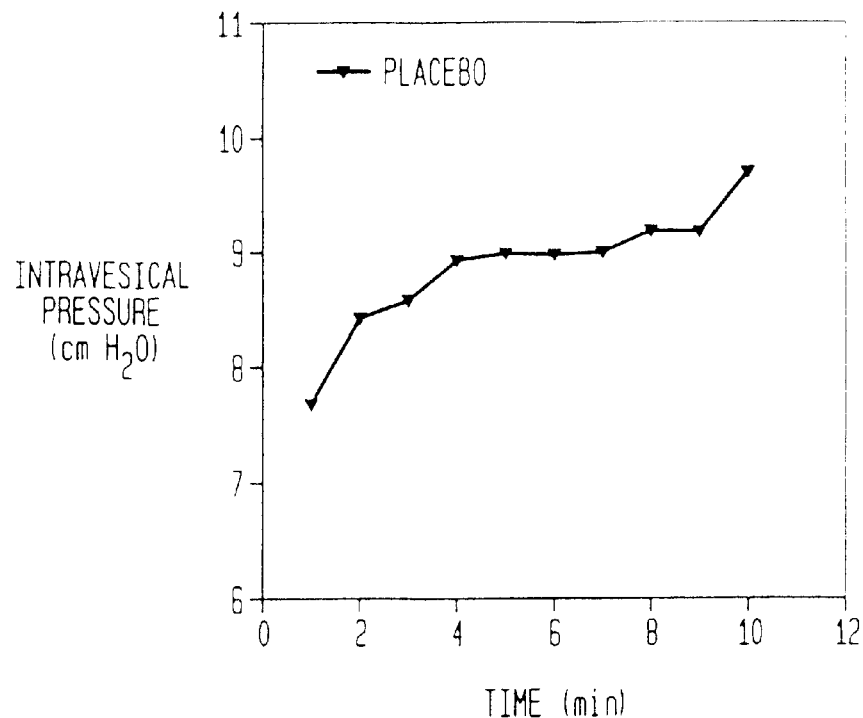
FIG. 13: Cystometry performed on rabbits with placebo inserts. Each point is the mean of cystometric curves performed on three individual rabbits.
Figure 14:
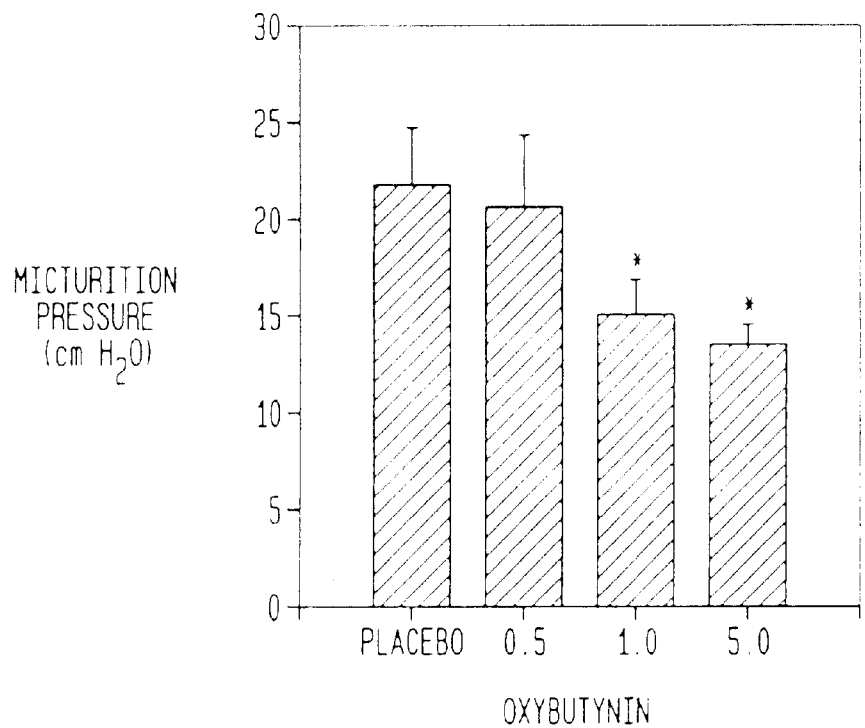
FIG. 14: Effect of the Oxybutynin implants on micturition pressure. Each bar is the mean +/− SEM of three individual rabbits. *=significantly different from placebo.

The vaginal insert had no effect on rabbit or bladder weight (FIG. 11). The analysis of the cystometries showed the typical effect of oxybutynin on the urinary bladder. There was a dose-dependent decrease in the cystometric pressures for the three oxybutynin groups (FIG. 12). The placebo cystometry is shown in FIG. 13. Simultaneously a dose-dependent decrease in micturition pressure for the oxybutynin groups was shown (FIG. 14). The micturition pressure for the 0.5 mg/day group was similar to the placebo group, whereas there was a significant decrease in the 1 and 5 mg/day oxybutynin groups.

Figure 15:
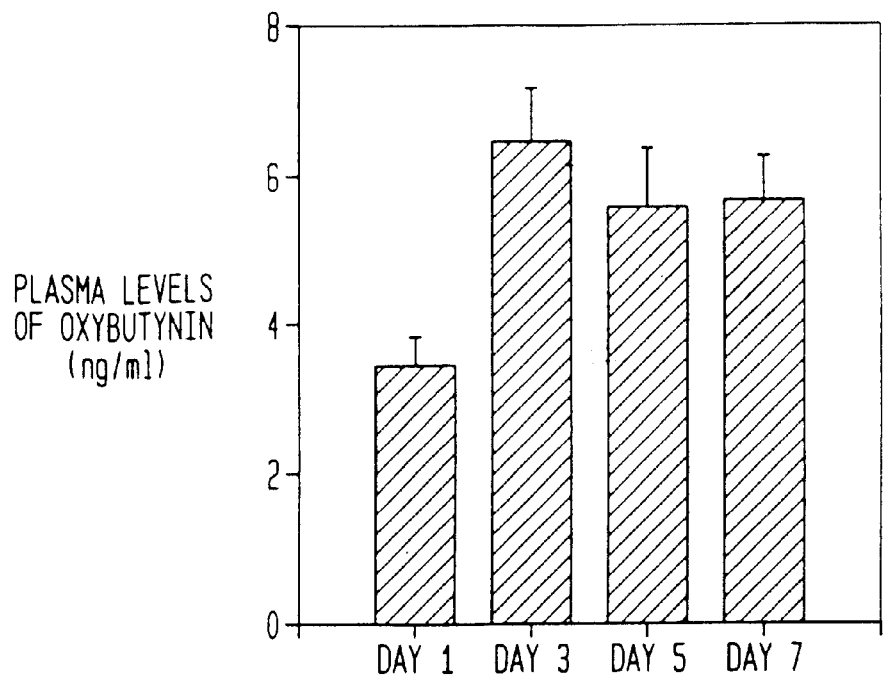
FIG. 15: Plasma values for rabbits with 0.5 mg/day inserts. Each bar is the mean +/− SEM of three individual rabbits.
Figure 16:
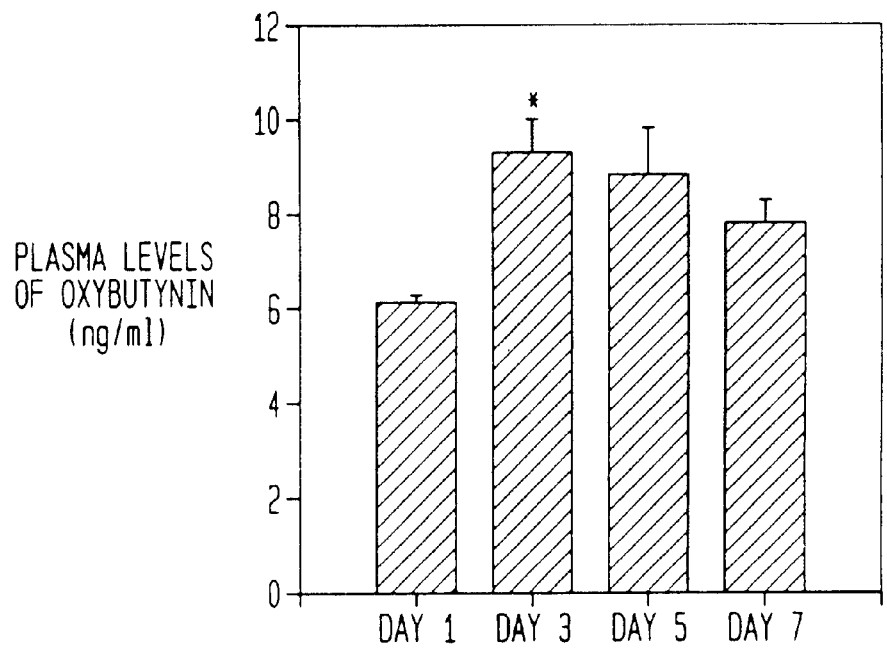
FIG. 16: Plasma values for rabbits with 1.0 mg/day inserts. Each bar is the mean +/− SEM of three individual rabbits significantly different from day 1.
Figure 17:
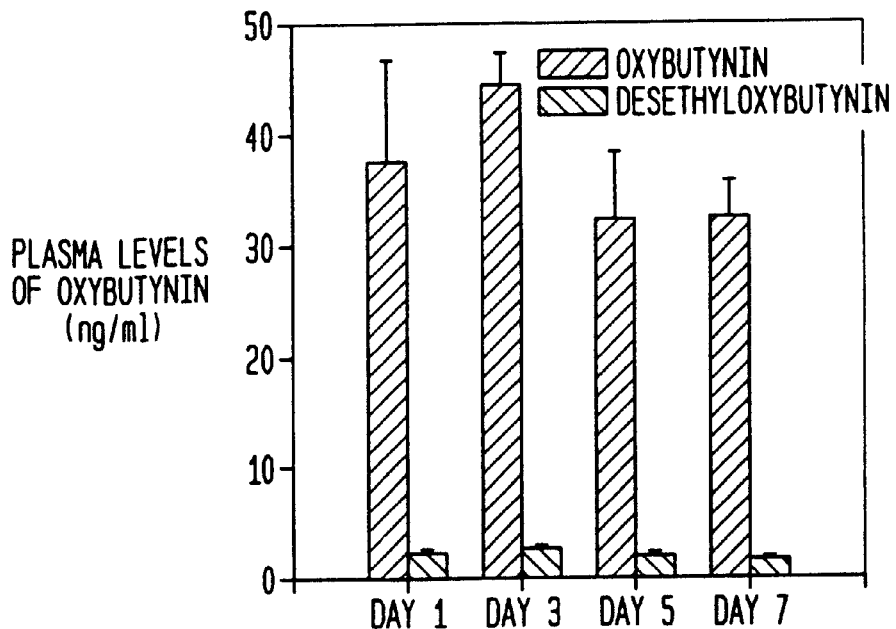
FIG. 17: Plasma values for oxybutynin and desethyfoxybutynin in rabbits with 5.0 mg/day inserts. Each bar is the mean +/− SEM of three individual rabbits.
Figure 18:
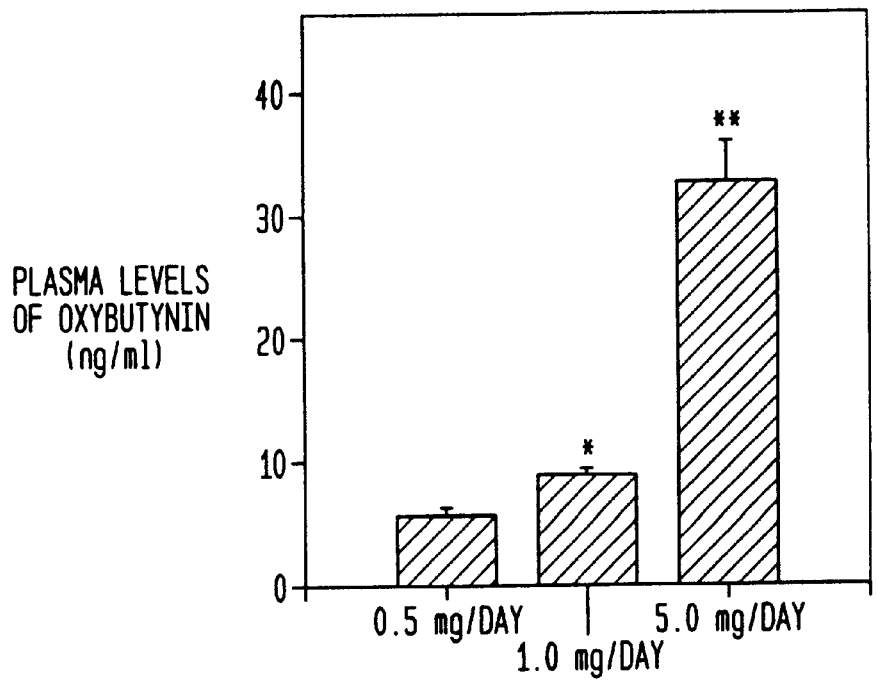
FIG. 18: Plasma values for rabbits with vaginal inserts after 7 days. Each bar is the mean +/− SEM of three individual rabbits. *=significantly different from 0.5 mg/day group; **=significantly different from 0.5 and 1.0 mg/day groups.

The plasma levels of oxybutynin for the three groups are shown in FIGS. 15–17. For the 0.5 and 1.0 mg/day groups, the plasma concentrations for desethyloxybutynin were below the level of detection. For the 0.5 mg/day and 1.0 mg/day group, there was an increase in the plasma concentrations between day 1 and 3, and a stable concentration between days 3 and 7. For the 5.0 mg/day group there were stable plasma values for both oxybutynin and desethyloxybutynin at all time periods (day 1–7). FIG. 18 shows the stable plasma concentrations for the three groups. The plasma concentration for the 1.0 mg/day group was significantly (approximately twice) that of the 0.5 mg/day group, the plasma concentration for the 5.0 mg/day group was significantly greater than the two other groups, and approximately 4 fold greater than the 1.0 mg/day group.

During the postmortem evaluation of the insert-contacted vaginal wall no irritation was observed in the area around the implants. There was however significant irritation (hematoma) in the area of the vagina where the speculum was placed to allow access to the upper vagina. Performing the insertion of the implant without use of a speculum avoided the irritation in control surgery.

Discussion

Oxybutynin is one of the most widely prescribed oral medications for the treatment of bladder instability. However, one of the major disadvantages to oral oxybutynin is the relative short half life, and the anticholinergic side effects. In many cases, the dosing schedule and side effects of this preparation significantly affect compliance. In order to improve compliance, several alternative dosing methods have been tried.

Intravesical instillation of oxybutynin can avoid the first pass metabolism and reduce systemic side effects [4,5], but is less convenient, and does not provide a method for continuous medication over a prolonged time period. Recently a controlled oxybutynin-release system for oral application was introduced. These studies have shown that a stable blood level under a controlled drug release system does not decrease the therapeutic effect, and allows a lower drug level. Also the appearance of side effects could be reduced [6–9].

In the current study, the placement of the vaginal inserts had no effect on rabbit or bladder weight, nor did the presence of the insert affect rabbit behavior (eating, sleeping, or drinking). The results of the cystometries performed one week after vaginal application of the inserts show the typical effect of oxybutynin on the urinary bladder. The dose related increased compliance, and decreased micturation pressure demonstrate that there was significant, dose-dependent and consistent absorption resulting in stable plasma oxybutynin levels.

Vaginal application of a drug release system allows a prolonged replacement interval. These attributes of this drug release system can improve the patient's convenience and compliance towards an oxybutynin based therapy of incontinence. Additionally it allows the possibility of a combined pessary-based therapy of a moderate stress- and drug-based therapy of motoric urge incontinence.

During the examination of the vaginal wall after a 1-week duration of direct contact to the insert no irritation could be shown.

Conclusion

The present study demonstrates a new method of an oxybutynin-release system, which creates a stable blood level and allows much longer application-free intervals. Thus, a device of the invention provides a new and useful alternative to traditional oral and intravesical application of oxybutynin. In particular, this study clearly demonstrates that a device of the invention releases a controlled, and consistent level oxybutynin, and that the stable plasma levels had significant effects on bladder compliance. There was no irritating effect by the insert on the vaginal wall after a one-week duration of placement. These results indicate that vaginal implants of oxybutynin are an excellent method for the chronic, dose dependent, delivery of the urologically effective agent.

Many other variations and modifications of the instant invention will be apparent to those skilled in the art without departing from the spirit and scope of the instant invention. The above-described embodiments are therefore, intended to be merely exemplary, and all such variations and modifications are intended to be included within the scope of the instant invention as defined in the appended claims.

Various publications are cited herein, the disclosures of which are incorporated by reference in their entireties:

A. Steers, W. D, Physiology of the urinary bladder. In Cambells Urology, (eds. Walsh, P. C., Retik, A. B., Starney, T. A., and Vaughan, E. D. Jr. ) Saunders, Phila., 1992, pp142–176.

B. Zderic, S. A., Levin, R. M., and Wein, A. J,: Voiding Function and Dysfunction: A—Relevant Anatomy, Physiology, and Pharmacology, and molecular biology. In: Adult and Pediatric Urology. Edited by J. Y. Gillenwater, J. T. Grayhack, S. S. Howards and J. D. Duckett, Chicago: Mosby Year Book Medical Publishers, Third Edition, pp. 1159–1219, 1996.

C. Uvin, R. M., Levin, S. S. and Wein, A. J.: Etiology of Incontinence: A review and hypothesis. Scandanavian J, Urol., Nephrol. 30 (Supp): 15–25, 1996.

D. Hampel, C., Wienhold, D., Benken, N., Eggersmann, C., and Thuroff, J. W. Definition of overactive bladder and epidemiology of urinary incontinence, Urology, 5 0:4–14, 1997.

E. Levin, R. M., Shofer, F. and Wein, A. J.: Cholinergic, adrenergic, and purinergic response of sequential strips of rabbit urinary bladder. J. Pharmacol. Exp., Ther. 212:536–540, 1980.

1. Thueroff, J. W., Bunke, B., Ebner, A., Faber, P., de Geeter, P., Hannapel, J., Heidler, H., Melchior, H.,Schaefer, W., Schweazer, T., Stoeckle, M.: Randomized double-blind, multicenter trial on treatment of frequency, urgency and incontinence related to detrusor hyperactivity: oxybutynin versus propantheline versus placebo. J.Urol, 145:913, 1991.

2. Levin, R. M., Wein, A. J.: Direct measurement of the anticholinergic activity of a series of pharmacological compounds on the canine and rabbit urinary bladder. S.Urol.;128:396–398, 1982.

3. Wein, A. J,: Pharmacologic options for the overactive bladder. Urology 51 (2A Suppl):43–7, 1998.

4. Buyse, G., Waldeck, K., Verpoorten, C., Bjoerk, H., Casaer, P., Andersson, K. E.: Intravesical oxybutynin for neurogenic bladder dysfunction: Less systemic side effects due to reduced first pass metabolism. J.Urol 160 (3Ptl):892–6, 1998.
5. Masad, C. A., Kogan, B. A., Trigo-Rocha, F. E.: The pharmacokinetics of intravesical and oral oxybutynin chloride. J. Urol., 148:595–597, 1992.
6. Goldenberg, M. M.: An extended-release formulation of oxybutynin chloride for the treatment of overactive urinary bladder. Clin Ther 21 (4),634–42, 1999.
7. Anderson, R. U., Mobley, D., Blank, B., Saltzstein, D., Susset, J. and Brown, J. S.: Once daily controlled versus immediate release oxybutynin Chloride for urinary incontinence. OROS Oxybutynin Study Group. J.Urol 161(6):1809–12, 1999.
8. Gupta, S. K,, Sathyan, G.: Pharmacokinetics of an oral once-a-day controlled-release oxybutynin formulation compared with immediate-release oxybutynin. J.Clin.Pharmacol. 39 (3):289–96, 1999.
9. Gupta, S. K., Sathyan, G., Lindemulder, E. A., Ho, P. L., Sheiner, L. B., Aarons, L.: Quantitative characterization of therapeutic index: Application of mixed-effects modeling to evaluate, oxybutynin dose-efficacy and dose-side effect relationships. Clin.Pharrnacol,Ther. 65(6); 672–84.

What is claimed is:

1. A device for locally delivering and controllably releasing oxybutynin to the cervical region of a female to treat urinary incontinence for a period of at least seven days in a single application, said device comprising:
   (a) a ring having a surface, and a bore which runs from said surface into said ring, wherein said ring comprises trifluoropropylmethyl/dimethyl siloxane elastomer, and said ring has a sufficient size such that it can be inserted into the vaginal canal of said female;
   (b) a pharmaceutical composition located within said bore, wherein said pharmaceutical composition comprises oxybutynin and an excipient;
   such that upon insertion of said ring into said vaginal canal, a therapeutically effective amount of oxybutynin is controllably released from the ring for a period of at least seven days in a therapeutically effective amount to treat the urinary incontinence.

2. The device of claim 1, wherein said bore intersects said surface of said ring twice.

3. The device of claim 1, wherein said ring comprises a first portion comprising trifluoropropylmethyl/dimethyl siloxane elastomer, and a second portion comprising a barium sulfate composite, trifluoropropylmethyl/dimethyl siloxane elastomer, or polydimethysiloxane, wherein said bore runs from the surface of said first portion into said first portion.

4. The device of claim 3, wherein said bore intersects said surface of said first portion twice.

5. The device of claim 3, wherein said second portion comprises trifluoropropylmethyl/dimethyl siloxane elastomer, and said bore further comprises a second bore which runs from the surface of said second portion into said second portion.

6. The device of claim 5, wherein said first bore intersects said surface of said first portion twife, and said second bore intersects said surface of said second portion twice.

7. The device of claim 3, wherein said ring further comprises at least two shields into which oxybutynin is insoluble, wherein said at least two shields are located between said first and second portions and intersect said first and second portions, such that said first and second portions do not come in contact.

8. The device of claim 7 wherein said at least two shields comprise polytetrafluoroethylene or a barium sulfate composite.

9. The device of claim 7, wherein said ring further comprises a third and fourth shields, and a third and forth portions, such that each shield lies between two portions so that no portion contacts any other portion, wherein at least one portion comprises trifluoropropylmethyl/dimethyl siloxane elastomer having said bore which runs from the surface of said at least one trifluoropropylmethyl/dimethyl siloxane elastomer portion into said at least one portion.

10. The device of claim 9, wherein said at least one trifluoropropylmethyl/dimethyl siloxane elastomer portion comprises a first portion and a second portion, and said bore comprises a first bore which runs from the surface of said first portion into said first portion, and a second bore which runs from the surface of said second portion into said second portion.

11. The device of claim 10, wherein said first bore intersects the surface of said first portion twice, said second bore intersects the surface of said second portion twice.

12. The device of claim 1, wherein said pharmaceutical composition comprises 60% by weight oxybutynin and 40% by weight excipient, wherein said excipient comprises tin catalyzed silicone polymer.

13. The device of claim 1 wherein said period of release is from at least seven days to about twenty-eight days.

14. The device of claim 1 wherein the oxybutynin is released at a rate of about 0.5 about 0.5 to about 5.0 mg/day.

15. The device of claim 13 wherein the oxybutynin is released at a rate of about 0.5 to about 5.0 mg/day.

16. A method of treating urinary incontinence in a female exhibiting urinary incontinence comprising providing a single application which controllably administers a therapeutically effective amount of oxybutynin intravaginally over a period of at least seven days comprising:
   (a) placing in the vagina of said female a device for controllably releasing oxybutynin, said device comprising:
      (1) a ring having a surface and a bore which runs from said surface into said ring, said ring comprising trifluoropropylmethyl/dimethyl siloxane elastomer that controllably releases oxybutynin by passage from said bore through said elastomer, said ring having a sufficient size such that it can be inserted into the vaginal canal of said female; and,
      (2) a pharmaceutical composition located within said bore, wherein said pharmaceutical composition comprises oxybutynin;
   wherein said oxybutynin is controllably released into the vagina in a therapeutically effective amount over a period of at least seven days to treat urinary incontinence in said female.

17. The method of claim 16 wherein said period of release is from at least seven days to about 28 days.

18. The method of claim 16 wherein said pharmaceutical composition comprises about 60% by weight oxybutynin and about 40% by weight an excipient.

19. The method of claim 18 wherein said excipient comprises tin catalyzed silicone polymer.

20. The method of claim 16 wherein said therapeutically effective amount 0.5 to about 5.0 mg/day.

21. The method of claim 17 wherein said oxybutynin is released at a rate of about 0.5 to about 5.0 mg/day.

* * * * *